(12) United States Patent
Sakaguchi et al.

(10) Patent No.: US 10,617,574 B2
(45) Date of Patent: Apr. 14, 2020

(54) ABSORBENT ARTICLE

(71) Applicant: UNICHARM CORPORATION, Ehime (JP)

(72) Inventors: Satoru Sakaguchi, Kagawa (JP); Maika Takahashi, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/306,899

(22) PCT Filed: May 9, 2017

(86) PCT No.: PCT/JP2017/017585
§ 371 (c)(1),
(2) Date: Dec. 4, 2018

(87) PCT Pub. No.: WO2018/003301
PCT Pub. Date: Jan. 4, 2018

(65) Prior Publication Data
US 2019/0321240 A1 Oct. 24, 2019

(30) Foreign Application Priority Data

Jun. 30, 2016 (JP) ................................ 2016-130258

(51) Int. Cl.
*A61F 13/494* (2006.01)
*A61F 13/49* (2006.01)
*A61F 13/551* (2006.01)

(52) U.S. Cl.
CPC .. *A61F 13/49466* (2013.01); *A61F 13/49019* (2013.01); *A61F 13/551* (2013.01); *A61F 2013/49493* (2013.01)

(58) Field of Classification Search
CPC .............. A61F 13/49466; A61F 13/49019
See application file for complete search history.

(56) References Cited

U.S. PATENT DOCUMENTS 5,904,675 A * 5/1999 Laux ................. A61F 13/49009
604/385.29
5,938,652 A * 8/1999 Sauer ................ A61F 13/49011
604/385.29

(Continued)

FOREIGN PATENT DOCUMENTS

EP 3061432 A1 8/2016
JP 2001-293029 A 10/2001
(Continued)

OTHER PUBLICATIONS

International Search Report for PCT/JP2017/017585; dated Jul. 25, 2017; 6 pages.

*Primary Examiner* — Susan S Su
(74) *Attorney, Agent, or Firm* — Hauptman Ham, LLP

(57) ABSTRACT

An absorbent article includes an absorbent main body, side flaps, leakage barriers, and an elastic member joined in between the side flaps in the absorbent main body, and stretchable and shrinkable in a width direction. Each leakage barrier includes a standing portion in which an outer side in the width direction is a fixed end, and an inner side in the width direction is a free end, and a supporting portion which is adjacent to one end portion in a longitudinal direction of the standing portion and overlaps with the elastic member in a thickness direction. The supporting portion is fixed to the absorbent main body by the heat welding portion. Each side flap is folded to the inner side in the width direction at a position of a folding line which passes through the supporting portion and extends along the longitudinal direction in a plan view.

5 Claims, 10 Drawing Sheets

(56) References Cited

U.S. PATENT DOCUMENTS

| | | | | |
|---|---|---|---|---|
| 6,258,076 | B1* | 7/2001 | Glaug | A61F 13/49466 604/385.01 |
| 6,336,922 | B1* | 1/2002 | VanGompel | A61F 13/49011 604/385.29 |
| 6,706,030 | B1* | 3/2004 | Okuda | A61F 13/49413 604/385.24 |
| 2003/0050616 | A1* | 3/2003 | Reynolds | A61F 13/49466 604/369 |
| 2004/0013850 | A1* | 1/2004 | Kling | A61F 13/15593 428/98 |
| 2004/0243079 | A1* | 12/2004 | Mitsui | A61F 13/49015 604/367 |
| 2004/0243090 | A1* | 12/2004 | Toyoshima | A61F 13/15203 604/389 |
| 2005/0222550 | A1 | 10/2005 | Mitsui et al. | |
| 2006/0025746 | A1* | 2/2006 | Sasaki | A61F 13/15203 604/386 |
| 2008/0269711 | A1* | 10/2008 | Sasayama | A61F 13/49011 604/385.09 |
| 2015/0126947 | A1 | 5/2015 | Stabelfeldt et al. | |
| 2017/0000656 | A1* | 1/2017 | Chatterjee | A61F 13/49466 |
| 2017/0000657 | A1* | 1/2017 | Chatterjee | A61F 13/49014 |
| 2018/0055698 | A1* | 3/2018 | Bishop | A61F 13/495 |
| 2018/0078429 | A1* | 3/2018 | Matsumura | A61F 13/49 |
| 2018/0271715 | A1* | 9/2018 | Back | A61F 13/49061 |

FOREIGN PATENT DOCUMENTS

| | | |
|---|---|---|
| JP | 2005-237984 A | 9/2005 |
| JP | 2005-297968 A | 10/2005 |
| JP | 2011-182860 A | 9/2011 |
| JP | 2014-237065 A | 12/2014 |
| JP | 5957160 B1 | 7/2016 |
| WO | 2005/097622 A1 | 10/2005 |

* cited by examiner

ABSORBENT ARTICLE

RELATED APPLICATIONS

The present application is a National Phase of International Application Number PCT/JP2017/017585 filed May 9, 2017 and claims priority to Japanese Application Number 2016-130258 filed Jun. 30, 2016.

TECHNICAL FIELD

The present invention relates to an absorbent article.

BACKGROUND ART

Absorbent articles such as a disposable diaper are known. An absorbent article, for example, includes an absorbent main body, a pair of side flaps which extend toward outer sides from both end portions in a width direction of the absorbent main body, an elastic member which is joined in between the pair of side flaps in the absorbent main body, and leakage barriers which extend along a longitudinal direction on both sides of a central portion in the width direction on one surface of the absorbent main body. In such an absorbent article, for example, the pair of side flaps are folded over the absorbent main body.

As the folding method of such an absorbent article, a folding method of a disposable diaper is disclosed in Patent Literature 1. In Patent Literature 1, the folding method is disclosed in which the pair of side flaps are folded at folding positions which extend along the longitudinal direction on the outer side of the both end portions in the width direction of the absorbent body. Further, the folding method is further disclosed in which thin portions are formed at positions in the width direction in the absorbent body, and the absorbent article is folded at folding positions which extend along the longitudinal direction and is positioned at the thin portions.

CITATION LIST

Patent Literature

PTL 1: Japanese Unexamined Patent Publication No. 2001-293029

SUMMARY OF INVENTION

Technical Problem

In an absorbent article, side flaps are folded along predetermined folding lines. However, since the absorbent body is not present at the end portion on one side, that is, on the dorsal side in the longitudinal direction of the absorbent main body, and such portion is formed mainly by thin materials such as a top sheet, a back sheet, (or an exterior sheet), etc., there may be a case in which folding creases are formed by the folding. In a case in which the folding creases are not present, the region on the dorsal side in the longitudinal direction of the absorbent article curves along the skin surface of the body of the wearer, and is to be in close contact with the skin surface, whereby the absorbent body also comes in close contact with the skin surface. As a result, excrement, for example, urine is prevented from leaking out to the dorsal side, and it is difficult for the odor of the excrement to leak out to the dorsal side. However, in a case in which the folding creases are present, there may be a case in which the portions at which the folding creases are present in the region on the dorsal side in the longitudinal direction of the absorbent article are separated from the skin surface of the body of the wearer due to the shape of the folding creases, and a portion of the dorsal side of the absorbent body is also separated from the skin surface, whereby a gap is formed between the absorbent article and the skin surface. Accordingly, there may be a case in which the excrement leaks out to the dorsal side, and the odor of the excrement leaks out to the dorsal side.

The object of the present invention is to provide an absorbent article which is capable of suppressing a gap between the absorbent article and the skin surface from being formed when being worn.

Solution to Problem

The absorbent article according to the present invention is as follows. (1) An absorbent article which includes a longitudinal direction, a width direction, and a thickness direction that are mutually orthogonal to each other, including: an absorbent main body; a pair of side flaps that extend to both outer sides in the width direction of the absorbent main body; and a pair of leakage barriers that are disposed in the absorbent main body, wherein a direction toward and a direction away from a longitudinal direction central axis of the absorbent main body in the width direction are respectively an inner side direction and an outer side direction, the absorbent article further including: an elastic member which is joined in between the pair of side flaps in the absorbent main body, and is stretchable and shrinkable in the width direction, wherein each of the pair of leakage barriers includes: a standing portion in which an outer side in the width direction is a fixed end, and an inner side in the width direction is a free end, and a supporting portion which is adjacent to one side in the longitudinal direction of the standing portion and overlaps with the elastic member in the thickness direction, the supporting portion is fixed to the absorbent main body by a heat welding portion, and each of the pair of side flaps is folded to an inner side in the width direction at a position of a folding line which passes through the supporting portion and extends along the longitudinal direction in a plan view.

In the present absorbent article, the position of the folding lines at which the pair of side flaps are folded and the supporting portion are overlapped with each other in the thickness direction (or in a plan view). The supporting portion is a portion of each of the leakage barriers, is fixed to the absorbent main body by the heat welding portion, and is overlapped with the elastic member. Accordingly, the position of the folding lines is provided at a portion in which the supporting portion including the heat welding portion, the elastic member and the absorbent main body are overlapped with each other, that is, a portion with rigidity. Consequently, the pair of side flaps of the absorbent article are folded at the position of the folding lines at respective portions with rigidity, whereby when the pair of side flaps of the absorbent article are expanded, the folding creases can be suppressed from being formed at the position of the folding lines. As a result, when the absorbent article is worn, the gap between the absorbent article and the skin surface can be suppressed from being formed. Accordingly, the leakage of the excrement to the dorsal side and the tendency of the odor of the excrement being easily leaked to the dorsal side can be prevented.

The absorbent article according to the present invention may be (2) the absorbent article according to the above mentioned (1), wherein the supporting portion includes the heat welding portion which has predetermined widths on both sides in the width direction at the folding line.

In the present absorbent article, the heat welding portion of the supporting portion has the predetermined widths on both sides of the folding line, whereby even when the folding lines along the longitudinal direction are shifted in the width direction to some extent, the folding lines can more reliably pass through the heat welding portion. That is, the folding lines can more reliably pass through the portions with rigidity, whereby the folding creases can be even more suppressed from being formed at the position of the folding lines. Accordingly, the gap between the absorbent article and the skin surface can be even more suppressed from being formed.

The absorbent article according to the present invention may be (3) the absorbent article according to the above mentioned (2), wherein the supporting portion includes the heat welding portion which is formed from one end portion to the other end portion in the longitudinal direction of the supporting portion.

In the present absorbent article, the heat welding portion of the supporting portion is continuously or intermittently formed from one end portion to the other end portion in the longitudinal direction of the supporting portion, whereby the rigidity of the supporting portion through which the folding lines pass can be even more increased, and thus the folding creases can be even more suppressed from being formed at the position of the folding lines. Accordingly, the gap between the absorbent article and the skin surface can be even more suppressed from being formed.

The absorbent article according to the present invention may be (4) the absorbent article according to any one of the above mentioned (1) to (3), wherein the elastic member includes a highly stretching portion which is positioned in a center in the width direction, and a pair of less stretching portions which are positioned on both sides in the width direction and stretch less than the highly stretching portion, and the folding line overlaps with the highly stretching portion in the thickness direction.

In the present absorbent article, the position of the folding lines and the highly stretching portion in the elastic member overlap with each other in the thickness direction. The highly stretching portion is a portion in which the elastic member is adhered in a highly stretched state when being adhered to the sheet of the absorbent main body, and shrinks with the sheet in a natural state so as to be in a bellows shape and to form a number of wrinkles. That is, the highly stretching portion is relatively increased in the basis weight and has a higher rigidity compared to the less stretching portion. Accordingly, the position of the folding lines is provided at such portions with rigidity. Consequently, by folding the pair of side flaps of the absorbent article at the position of the folding lines at respective portions with rigidity, the folded portions can easily transition from the folded state to the expanded state when being worn, whereby the gap between the absorbent article and the skin surface can be suppressed from being formed. Accordingly, the leakage of the excrement to the dorsal side and the tendency of the odor of the excrement being easily leaked to the dorsal side can be prevented.

The absorbent article according to the present invention may be (5) the absorbent article according to any one of the above mentioned (1) to (4), wherein the folding line overlaps with at least a portion of an absorbent body in the absorbent main body in the thickness direction.

In the present absorbent article, the position of the folding lines and at least a portion of the absorbent body in the absorbent main body are overlapped with each other in the thickness direction. The absorbent body is somewhat separated from the end portion in the longitudinal direction in the dorsal side region of the absorbent main body, however, by the absorbent body also being bent when the side flaps are folded, the bending of the end portion in the longitudinal direction in the dorsal side region of the absorbent main body, in which the folding creases are easily formed, can be moderate. Accordingly, the suppression of the folding creases by making the folding lines pass through the supporting portion can be assisted. Consequently, the gap between the absorbent article and the skin surface can be suppressed from being formed. Accordingly, the leakage of the excrement to the dorsal side and the tendency of the odor of the excrement being easily leaked to the dorsal side can be prevented.

The absorbent article according to the present invention may be (6) the absorbent article according to any one of the above mentioned (1) to (5), further including a joining target portion which is joined to the other region in the longitudinal direction in the absorbent main body, and is to be a target of joining the pair of side flaps when being worn, wherein the folding line overlaps with the joining target portion in the thickness direction.

In the present absorbent article, the position of the folding lines and the joining target portion in the other region in the longitudinal direction in the absorbent main body, that is, the ventral side region are overlapped with each other in the thickness direction. That is, the folding lines (the folding positions) are provided at portions with rigidity. Consequently, by folding the pair of side flaps of the absorbent article at the position of the folding lines at respective portions with rigidity, the folded portions can easily transition from the folded state to the expanded state when being worn, whereby the gap between the absorbent article and the skin surface can be suppressed from being formed. Accordingly, the leakage of the excrement to the dorsal side and the tendency of the odor of the excrement being easily leaked to the dorsal side can be prevented.

The absorbent article according to the present invention may be (7) the absorbent article according to any one of the above mentioned (1) to (6), wherein the absorbent main body includes a top sheet, a back sheet, and an absorbent body which is positioned in between the top sheet and the back sheet, and the elastic member is positioned closer to a top sheet side than the absorbent body, in between the top sheet and the back sheet, overlaps with the absorbent body in the thickness direction, and is not joined to the absorbent body.

In the present absorbent article, the elastic member is positioned closer to the top sheet side than the absorbent body, overlaps with the absorbent body in the thickness direction, however, is not joined to the absorbent body. Accordingly, the elastic member can shrink without receiving influence of the absorbent body. Since the elastic member is positioned close to the end portion in the longitudinal direction in the dorsal side region of the absorbent main body, in which the folding creases are easily formed, the folding creases can be suppressed by the shrinkage of the elastic member when the absorbent article is worn, whereby the gap between the absorbent article and the skin surface can be suppressed from being formed.

Advantageous Effect of Invention

According to the present invention, an absorbent article which is capable of suppressing a gap between the absorbent article and the skin surface from being formed when being worn can be provided.

DESCRIPTION OF EMBODIMENTS

The absorbent article according to the embodiment of the present invention will be explained with reference to the drawings, with a tape type (an open type) disposable diaper taken as an example. However, the types and usage of the absorbent article of the present invention are not limited to the example, and the present invention can be applied to other types and usage of the absorbent article, for example, a pants type disposable diaper, without departing from the scope of the subject matter of the present invention.

First Embodiment

Figure 1:
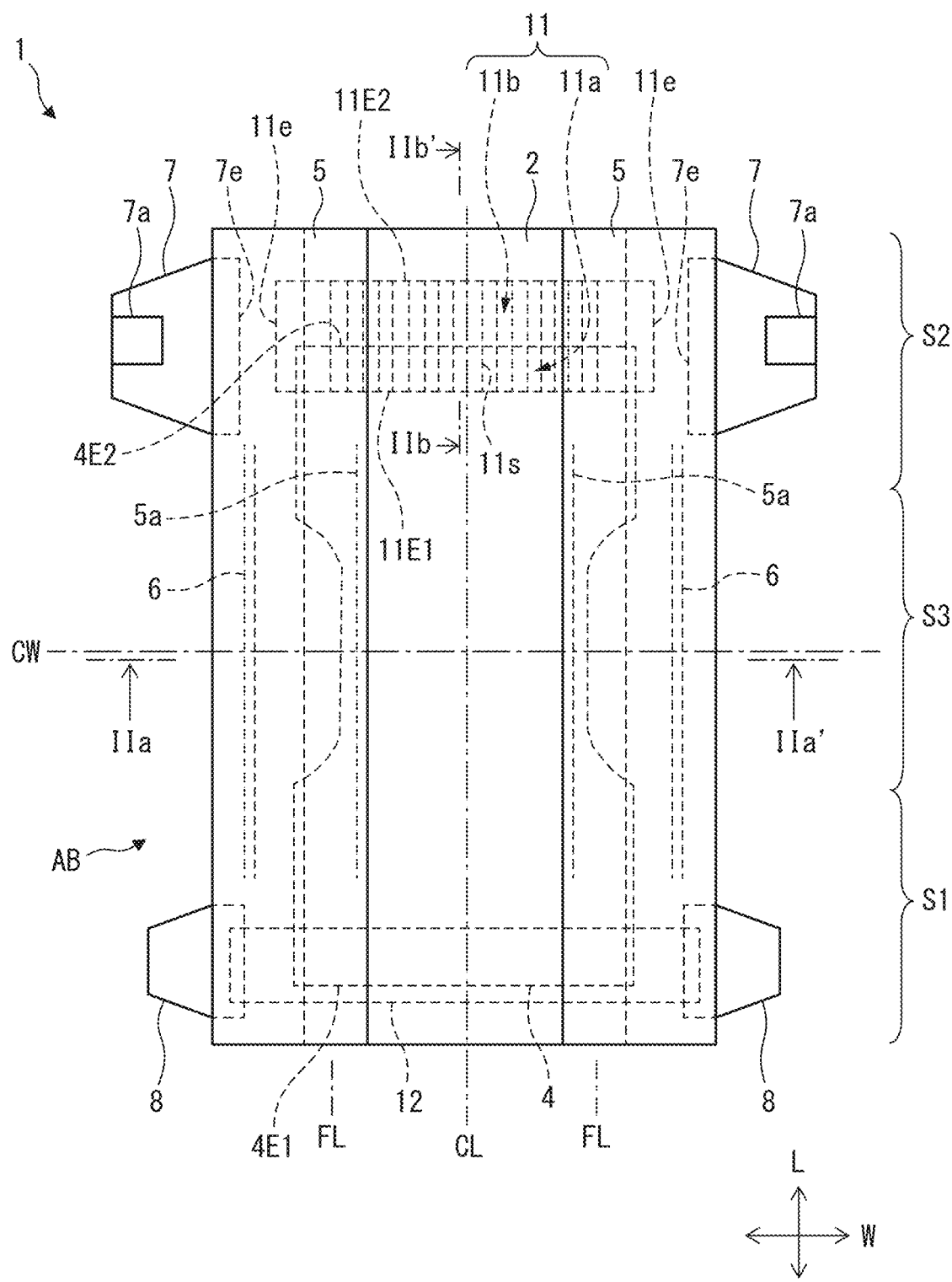
FIG. 1 is a view showing an absorbent article according to a first embodiment.
Figure 2A:
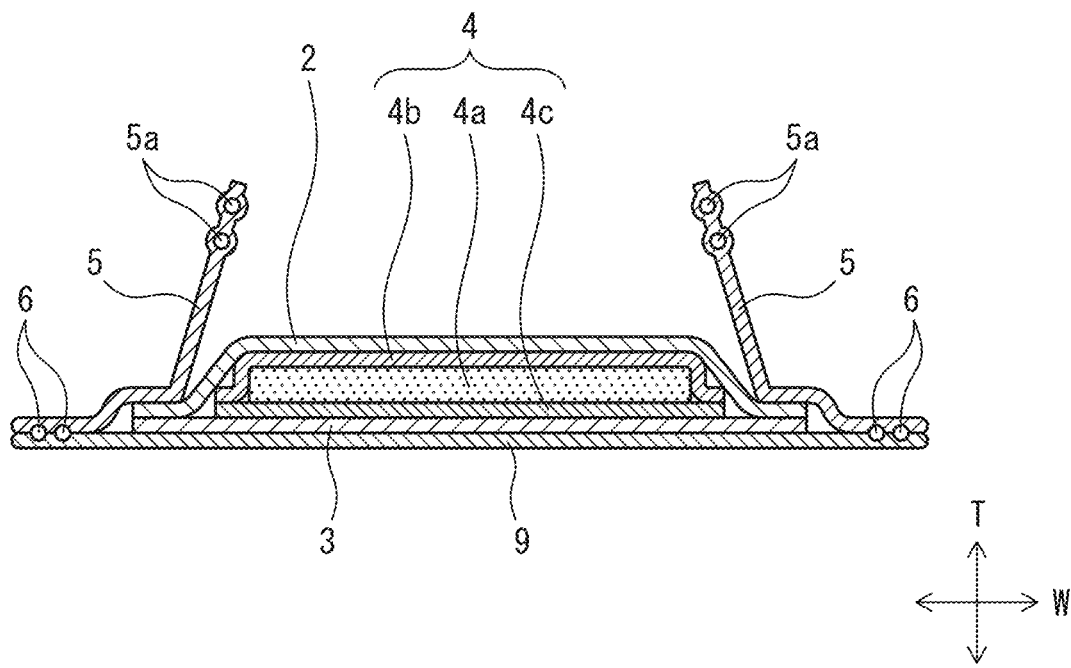
FIG. 2A and FIG. 2B are views showing the absorbent article according to the first embodiment.
Figure 2B:
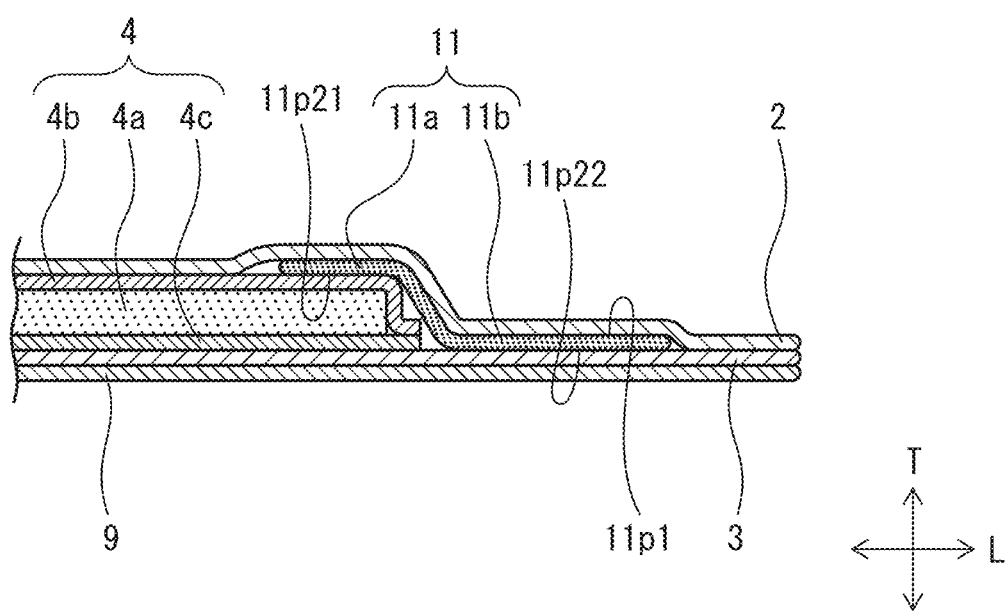

The first embodiment will be explained. FIGS. 1 and 2 are views showing the absorbent article 1 (a disposable diaper) according to the present embodiment. Note that FIG. 1 is a plan view in a state in which the absorbent article 1 is opened and expanded, FIG. 2A is a sectional view along the line IIa-IIa' shown in FIG. 1, and FIG. 2B is a sectional view along the line IIb-IIb' shown in FIG. 1. The absorbent article 1 includes a longitudinal direction L, a width direction W which is orthogonal to the longitudinal direction L, and a thickness direction T which is orthogonal to the longitudinal direction L and to the width direction W, and further includes a central axis (a longitudinal direction central axis) CL which passes through the center in the width direction W and extends in the longitudinal direction L, and a central axis (a width direction central axis) CW which passes through the center in the longitudinal direction L and extends in the width direction W. Further, viewing the absorbent article 1 which is opened and expanded in a flat manner, from the upper surface side in the thickness direction, is referred to as "a plan view". "A skin side" and "a non-skin side" respectively mean the sides relatively closer to the skin surface of the wearer and further to the skin surface, in the thickness direction of the absorbent article 1, when the absorbent article 1 is worn. The directions toward and away from the central axis CL are respectively referred to as the inner side direction and the outer side direction in the width direction W. The directions toward and away from the central axis CW are respectively referred to as the inner side direction and the outer side direction of the longitudinal direction L. These definitions are also applied to the materials and members which configure the absorbent article 1. Note that FIG. 1 is a diagram in which the absorbent article 1 is viewed from the skin surface side.

The absorbent article 1 includes, in the longitudinal direction L, a dorsal side waist region S2 which corresponds to the waist on the dorsal side of the wearer, a ventral side waist region S1 which corresponds to the waist on the ventral side of the wearer, and a crotch region S3 which corresponds to the crotch of the wearer and is positioned in between the dorsal side waist region S2 and the ventral side waist region S1. The absorbent article 1 includes an absorbent main body AB which extends in the longitudinal direction L from the dorsal side waist region S2 to the ventral side waist region S1, a pair of side flaps 7, 7 which extend toward the outer side from the both end portions in the width direction W of the absorbent main body AB, in the dorsal side waist region S2, and a pair of leakage barriers 5, 5 which are positioned on one surface of the absorbent main body AB. The absorbent article 1 is worn as a diaper, for example, by a pair of fastening tapes 7a, 7a of the pair of side flaps 7, 7 in the dorsal side waist region S2 being connected to a joining target member 12 on the center portion of the absorbent main body AB in the width direction W in the ventral side waist region S1. The crotch region S3 may be constricted toward the inner side in the width direction W. The directions toward the dorsal side waist region S2 and toward the ventral side waist region S1 in the longitudinal direction L are also respectively referred to as a rear side (or a dorsal side) direction and a front side (or a ventral side) direction.

The absorbent main body AB of the absorbent article 1 includes a top sheet 2, a back sheet 3, and an absorbent body 4. The top sheet 2 is a liquid permeable sheet which is positioned on the skin side of the wearer. As the top sheet 2, for example, an arbitrary liquid permeable sheet may be mentioned, such as a liquid permeable nonwoven fabric, a liquid permeable woven fabric, a synthetic resin film in which liquid permeable holes are formed, a composite sheet of the above mentioned sheets, etc. The back sheet 3 is a liquid impermeable sheet which is positioned on the non-skin side of the wearer. As the back sheet 3, for example, an arbitrary liquid impermeable sheet may be mentioned, such as a liquid impermeable nonwoven fabric, a synthetic resin film, a composite sheet of the above mentioned sheets, SMS nonwoven fabric, etc. The absorbent body 4 is a liquid absorbent and liquid retainable material which is positioned in between the top sheet 2 and the back sheet 3, and in the present embodiment, the absorbent body 4 includes an absorbent body core 4a and core wrapping sheets 4b, 4c which are wrapped around the absorbent body core 4a. As the absorbent body 4, pulp fibers, synthetic fibers, absorbent polymers, etc., may be mentioned. The absorbent body 4, the top sheet 2 and the back sheet 3 are respectively joined by an adhesive agent, and the top sheet 2 and the back sheet 3 are joined to each other by being applied with an adhesive agent at the peripheral portions thereof. The adhesive agent for the joining, which is applied in between the top sheet 2, the absorbent body 4 and the back sheet 3, may be a known material which is generally used in the absorbent article 1, for example, a thermoplastic adhesive agent.

The absorbent article 1 further includes a pair of leakage barriers 5, 5, leg portion elastic members 6, 6, and an exterior sheet 9. The pair of leakage barriers 5, 5 are liquid impermeable sheets which are positioned on both sides of the center portion in the width direction W, on one surface of the top sheet 2, and prevents liquid leakage in the width direction W. The pair of leakage barriers 5, 5 extend along the longitudinal direction L, and are separated from each other in the width direction W. In each of the pair of leakage barriers 5, 5, the outer side portion in the width direction W is fixed to the absorbent main body AB by heat welding, etc., so as to be a fixed end, and the inner side end portion in the width direction W is a free end which forms a stretchable and shrinkable gather portion. In the vicinity of each of the free ends of the pair of leakage barriers 5, 5, for example, two linear elastic bodies 5$a$ such as a rubber, are disposed which extend along the longitudinal direction L. The leg portion elastic members 6 are elastic materials such as a rubber, which stretch and shrink, in the longitudinal direction L, the both sides in the width direction W of the crotch region S3 that comes in contact with the thigh portion of the wearer. The exterior sheet 9 is a hydrophobic sheet which is positioned on the non-skin side of the back sheet 3, so as to reinforce the back sheet 3 and to improve the texture thereof. The exterior sheet 9 is mutually joined to the pair of leakage barriers 5, 5 at the peripheral portions thereof by an adhesive agent, etc., in a state of being joined to the non-skin side of the back sheet 3. The materials of the leakage barriers 5 and the exterior sheet 9 are not particularly limited, and for example, as the leakage barriers 5 and the exterior sheet 9, the materials of the back sheet 3 may be mentioned.

The absorbent article 1 further includes an elastic member 11 in the dorsal side waist region S2. The elastic member 11 is a sheet-like member which has a stretching and shrinking property in the width direction W, disposed in between the pair of side flaps 7, 7 in the width direction W, and functions for example, as a waist gather. The elastic member 11 is joined to the top sheet 2 or to the back sheet 3 by an adhesive agent, at either one of the positions of, the position between the top sheet 2 and the back sheet 3 in the dorsal side waist region S2, the skin side surface of the top sheet 2, and the non-skin side surface of the back sheet 3. In the present embodiment, the elastic member 11 is joined in between the top sheet 2 and the back sheet 3. The material of the elastic member 11 is not particularly limited as long as the material is stretchable and shrinkable, and the material may be stretchable and shrinkable due to the property thereof, due to the shape thereof, or due to being in combination with an elastic member. As the material of the elastic member 11, for example, a film elastic member such as a polyurethane film, polystyrene film, etc., a sheet-like elastic member composed of a styrene type rubber, an olefin type rubber, or a urethane type rubber, etc., and of a nonwoven fabric, or paper, etc., and stretchable and shrinkable nonwoven fabric, etc., may be mentioned. Further, the material of the elastic member 11 may also be a thread rubber-like elastic member, other than the stretchable and shrinkable sheet.

In the present embodiment, the elastic member 11 is disposed in between the absorbent body 4 and the top sheet 2 in the thickness direction T, and at least a portion thereof overlaps with and is in contact with the absorbent body 4. That is, in a plan view, in the longitudinal direction L, an end portion 4E2 in the rear side direction of the absorbent body 4 is positioned in between an end portion 11E1 in the front side direction of the elastic member 11 and an end portion 11E2 in the rear side direction thereof. Further, the elastic member 11 includes a front side portion 11$a$ which is positioned in between the end portion 11E1 and the end portion 4E2, and a rear side portion 11$b$ which is positioned in between the end portion 11E2 and the end portion 4E2. The front side portion 11$a$ is a portion on the front side in the longitudinal direction L, overlaps with and is in contact with the absorbent body 4 in the thickness direction T (except for the both end portions in the width direction W), and is positioned closer to the skin side than the absorbent body 4. On the other hand, the rear side portion 11$b$ is a portion on the rear side in the longitudinal direction L, which does not overlap with the absorbent body 4 in the thickness direction T, and overlaps with and is in contact with the back sheet 3. In the elastic member 11, a non-skin side surface 11$p21$ of the front side portion 11$a$ is in contact with the absorbent body 4, however, is not joined to the absorbent body 4, and accordingly, is not adhered for example by an adhesive agent, etc. On the other hand, a non-skin side surface 11$p22$ of the rear side portion 11$b$ is not in contact with the absorbent body 4, however, is in contact with the back sheet 3 and is joined to the back sheet 3, and accordingly, is adhered for example by an adhesive agent, etc. Further, a skin side surface 11$p1$ of the front side portion 11$a$ and the rear side portion 11$b$ is in contact with the top sheet 2 and is joined to the top sheet 2, and accordingly, is adhered for example by an adhesive agent, etc. In these manners, the elastic member 11 and the absorbent body 4 overlap with each other in the thickness direction T, however, are not joined to each other, that is, the elastic member 11 and the absorbent body 4 are not joined to each other by an adhesive agent, etc. Accordingly, the elastic member 11 and the absorbent body 4 are capable of relatively and mutually moving from each other. Consequently, the elastic member 11 can easily be stretched toward the outer side in the width direction W, and can easily be shrunk toward the inner side accordingly. Incidentally, as for the both end portions in the width direction W in the front side portion 11$a$ (which are the portions that do not overlap with the absorbent body 4 in the thickness direction T), the skin side surface thereof is in contact with the top sheet 2 and is joined to the top sheet 2, whereas the non-skin side surface thereof is in contact with the back sheet 3 and is joined to the back sheet 3. Incidentally, the present embodiment shows, as described above, a case in which the elastic member 11 and the absorbent body 4 are partially not joined to each other (that is, the non-skin side surface 11$p21$ of the front side portion 11$a$ and the absorbent body 4 are not joined to each other), however, in the opposite manner, the elastic member 11 and the absorbent body 4 may be configured so as not to have any portions that are not joined to each other.

Each of the pair of side flaps 7, 7 which extends toward the outer side from the both end portions in the width direction W of the absorbent main body AB is a sheet-like member which has a stretching and shrinking property in the width direction W, and one of and the other of the pair of side flaps 7, 7 are respectively formed at one end portion and the other end portion in the width direction W of the absorbent main body AB. The pair of side flaps 7, 7, for example, function as stretchable and shrinkable side flaps so as to connect the dorsal side waist region S2 to the ventral side waist region S1 at the time of wearing. Further, since the pair of side flaps 7, 7 have the stretching and shrinking property in the width direction W, the pair of side flaps 7, 7 can stretch the both end portions in the width direction W of the absorbent main body AB, so as to press the absorbent body 4 inside the absorbent main body AB toward the skin side. The material of each of the pair of side flaps 7, 7 is not particularly limited as long as the material is stretchable and shrinkable, and the material may be stretchable and shrinkable due to the property thereof, due to the shape thereof, or due to being in combination with an elastic member. As the material of each of the pair of side flaps 7, 7, for example, materials similar to those for the elastic member 11 may be used. Each of the pair of side flaps 7, 7 overlaps with the absorbent body 4 in the width direction W. In the present embodiment, a portion of each of the pair of side flaps 7, 7 overlaps with the absorbent body 4 in the width direction W. Accordingly, it is easier for each of the pair of side flaps 7, 7 to transfer the shrinking force thereof to the absorbent body 4, so as to more strongly press the absorbent body 4 toward the skin side.

Each of the pair of side flaps 7, 7 is disposed so as to protrude toward the both outer side in the width direction W in the dorsal side waist region S2, and is attached by an adhesive agent to either one of the positions of, the position in between the top sheet 2 (or the leakage barriers 5) and the back sheet 3 (or the exterior sheet 9) in the dorsal side waist region S2, the skin side surface of the top sheet 2 (or the leakage barriers 5), and the non-skin side surface of the back sheet 3 (or the exterior sheet 9). However, each of the pair of side flaps 7, 7 may be formed of an extended portion of at least one of the top sheet 2 (or the leakage barriers 5) and the back sheet 3 (or the exterior sheet 9). In the present embodiment, each of the pair of side flaps 7, 7 is formed of a member different from the top sheet 2, the leakage barriers 5, the back sheet 3, and the exterior sheet 9, and is disposed in between the leakage barriers 5 and the exterior sheet 9.

Each of the pair of side flaps 7, 7 includes a fastening tape 7a so as to be connected to a joining target member 12 of the ventral side waist region S1 when being worn. In the present embodiment, the entirety of the fastening tape 7a overlaps with the elastic member 11 when viewed from the width direction W. Accordingly, when the pair of side flaps 7, 7 are stretched, whereby the fastening tape 7a of each side flap 7 is attached to the joining target member 12, the shrinking force of the side flap 7 and the shrinking force of the elastic member 11 cooperate in between the fastening tapes 7a, and thus the absorbent body 4 can be even more strongly pressed toward the skin side.

The elastic member 11 is disposed in between the pair of side flaps 7, 7. That is, the elastic member 11 and the pair of side flaps 7, 7 are disposed so that at least portions thereof overlap with each other when viewed from the width direction W. In other words, at least a portion of the projection to the central axis CL of an edge side 11e along the longitudinal direction L which is on the outer side in the width direction W in the elastic member 11 and at least a portion of the projection to the central axis CL of an edge side 7e along the longitudinal direction L which is on the inner side in the width direction W in each of the pair of side flaps 7, 7 are overlapped with each other. Accordingly, the fitting property of the dorsal side waist region S2 can be improved when the absorbent article 1 is worn. Further, in the width direction W, the elastic member 11 and each of the pair of side flaps 7, 7 may be separated from each other, or may be partially overlapped with each other. In the present embodiment, in the width direction W, the elastic member 11 and each of the pair of side flaps 7, 7 are separated from each other. Accordingly, the portion of the absorbent main body AB which does not stretch or shrink, positioned in between the elastic member 11 and each of the pair of side flaps 7, 7, does not stretch but pulls the both end portions in the width direction W thereof, whereby the absorbent body 4 can be even more strongly pressed toward the skin side.

The absorbent article 1 further includes the joining target member 12 and a pair of protruded portions 8, in the ventral side waist region S1. The joining target member 12 is a sheet which is the target of the fastening tapes 7a of the pair of side flaps 7, 7 to be connected thereto, and for example, in a case in which the fastening tape 7a is the hooks of a hook-and-loop fastener, the joining target member 12 functions as the loops of the hook-and-loop fastener, and in a case in which the fastening tape 7a is an adhesive tape, the joining target member 12 is a sheet which is capable of being adhered by the adhesive tape. The joining target member 12 is attached, for example by an adhesive agent, at a position of the non-skin side surface of the exterior sheet 9 in the ventral side waist region S1. The pair of protruded portions 8, 8 are sheets so as to connect the ventral side waist region S1 to the dorsal side waist region S2 when being worn, and function as side flaps. The pair of protruded portions 8 are disposed so as to protrude toward the both outer side in the width direction W of the ventral side waist region S1, and are attached by an adhesive agent to either one of the positions of, the position in between the top sheet 2 (or the leakage barriers 5) and the back sheet 3 (or the exterior sheet 9) in the ventral side waist region S1, the skin side surface of the top sheet 2 (or the leakage barriers 5), and the non-skin side surface of the back sheet 3 (or the exterior sheet 9). However, each of the pair of protruded portions 8, 8 may be formed by an extended portion of at least one of the top sheet 2 (or the leakage barriers 5) and the back sheet 3 (or the exterior sheet 9). In the present embodiment, each of the pair of protruded portions 8, 8 is formed by a member different from the top sheet 2, the leakage barriers 5, the back sheet 3, and the exterior sheet 9, and is disposed in between the leakage barriers 5 and the exterior sheet 9. The material of the protruded portions 8 is not particularly limited, and for example, the materials of the top sheet 2 or the back sheet 3 may be mentioned. Note that the protruded portions 8 may not be provided.

Figure 3:
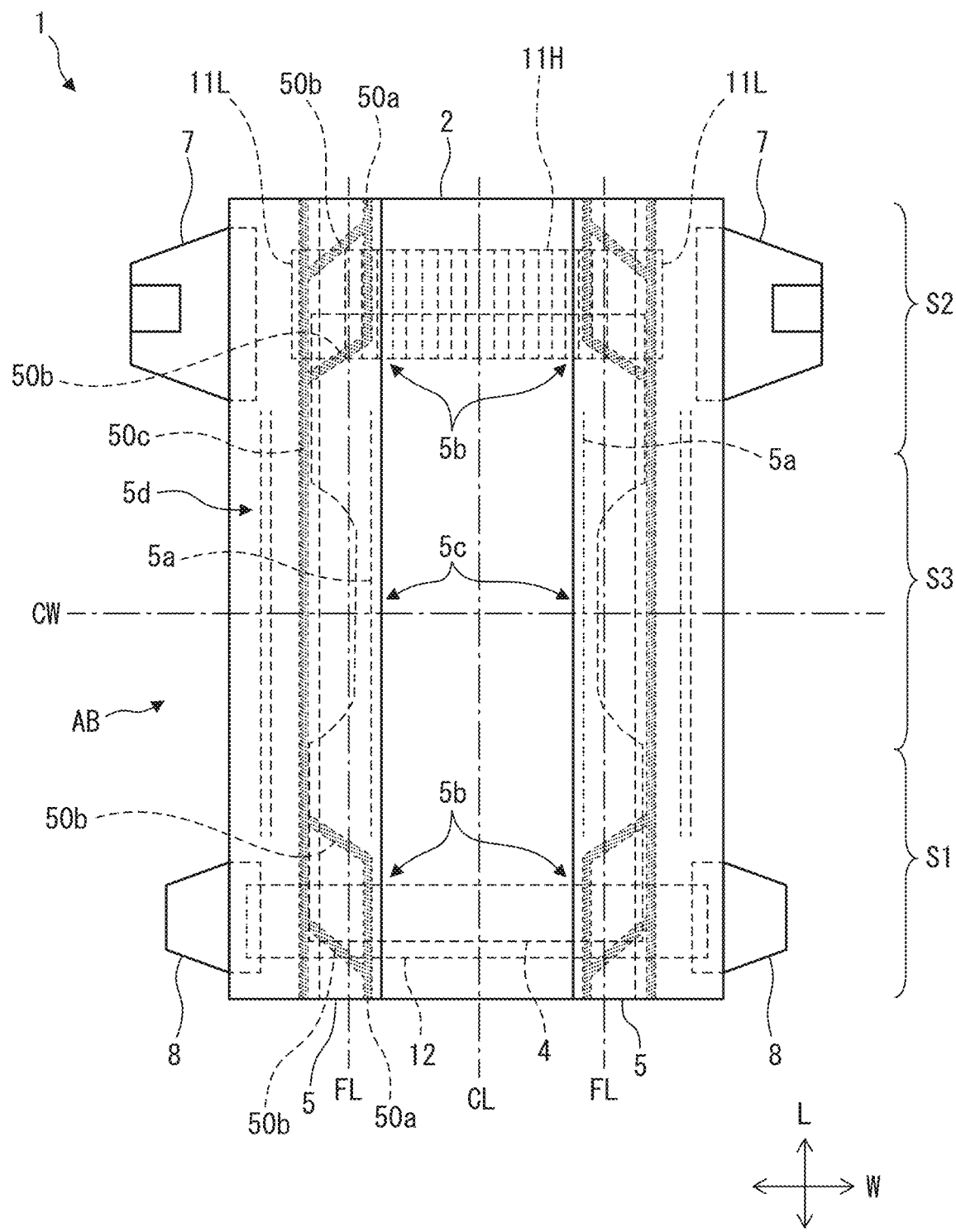
FIG. 3 is a view showing a junction of leakage barriers in the absorbent article according to the first embodiment.

Next, the pair of leakage barriers 5, 5 are further explained. FIG. 3 is a view explaining a junction between the absorbent main body AB and the pair of leakage barriers 5, 5, and to be more specific, FIG. 3 shows the configuration pertaining to the pair of leakage barriers 5, 5 in FIG. 1 in a detailed manner. Each leakage barrier 5 includes a standing portion 5c, a pair of supporting portions 5b, and a joining portion 5d. The standing portion 5c is a portion in the center on the inner side in the width direction W of each leakage barrier 5, in which the outer side in the width direction W is a fixed end, and the inner side in the width direction W is a free end. The standing portion 5c includes a linear elastic body 5a which extends along the longitudinal direction L at the inner side end portion in the width direction W, and stands up toward the skin side by the shrinkage of the elastic body 5a when the absorbent article 1 is worn, so as to form a three dimensional gather. The pair of supporting portions 5b are portions which are respectively adjacent to one of and the other of the end portions in the longitudinal direction L of the standing portion 5c. The pair of supporting portions 5b are fixed to the absorbent main body AB at least by the heat welding portion 50. Accordingly, the pair of supporting portions 5b retain the standing portion 5c at the one of and the other of the end portions in the longitudinal direction L of the standing portion 5c. The supporting portion 5b on the dorsal side among the pair of supporting portions 5b overlaps with the elastic member 11 in the thickness direction T. The joining portion 5d is a portion which is adjacent to the outer side end portions in the width direction W of the standing portion 5c and the pair of supporting portions 5b. The joining portion 5d is fixed to the absorbent main body AB at least by the heat welding portion 50. Accordingly, the joining portion 5d retains the standing portion 5c at the outer side end portion in the width direction W of the standing portion 5c. Further, the joining portion 5d is fixed to the peripheral portions of the absorbent main body AB and of the exterior sheet 9 by an adhesive agent.

Next, the heat welding portion 50 which is formed by heat welding in the pair of supporting portions 5b and in the joining portion 5d will be explained. The heat welding portion 50 is a portion which joins the leakage barriers 5 at least to the absorbent main body AB, and is formed by heat-welding the leakage barriers 5 and the absorbent main body AB in the thickness direction T. The forms (shapes) of the heat welding portion may be in a linear (including curves) continuous manner, or may be in a form in which a plurality of patterns of a circle, an ellipse, a rectangle, a parallelogram, a polygon, etc., are arranged intermittently in a longitudinal direction and/or in a lateral direction in a linear (including curves) manner, or may have a substantially lattice pattern. In the present embodiment, the heat welding portion has a form in which a plurality of patterns of a rectangle or a parallelogram are arranged intermittently in a linear manner.

In the present embodiment, the heat welding portion 50 includes at least a heat welding portion (a longitudinal direction heat welding portion) 50a, a heat welding portion (a width direction heat welding portion) 50b, and a heat welding portion (an outer side heat welding portion) 50c. The heat welding portion 50a is a heat welding portion which extends continuously or intermittently and substantially along the longitudinal direction L (or may be oblique with respect to the longitudinal direction L) in the supporting portion 5b, and for example is positioned on the inner side in the width direction W of the supporting portion 5b. The heat welding portion 50b is a heat welding portion which extends continuously or intermittently and substantially along the width direction W (or may be oblique with respect to the width direction W) in the supporting portion 5b, and for example is positioned at substantially both end portions in the longitudinal direction L of the supporting portion 5b. The heat welding portion 50c is a heat welding portion which extends continuously or intermittently and substantially along the longitudinal direction L (or may be oblique with respect to the longitudinal direction L) in the joining portion 5d, and for example is positioned on the inner side in the width direction W of the joining portion 5d. The heat welding portions 50a, 50b fix mainly the supporting portion 5b of the leakage barriers 5 to the absorbent main body AB. In the present embodiment, a portion in the longitudinal direction L of the elastic member 11 and the supporting portion 5b are positioned on the opposite sides to each other with the top sheet 2 therebetween, and the heat welding portion 50b fixes a portion of the top sheet 2 which corresponds to the above mentioned portion in the longitudinal direction L of the elastic member 11 to the supporting portion 5b. Preferably, the both end portions in the longitudinal direction L of the elastic member 11 and the supporting portion 5b are positioned on the opposite sides to each other with the top sheet 2 therebetween, and the heat welding portion 50b fixes the portions in the top sheet 2 which correspond to the above mentioned both end portions in the longitudinal direction L of the elastic member 11 to the supporting portion 5b, and does not fix the portion which corresponds to the center portion thereto.

In the present embodiment, the elastic member 11 includes a highly stretching portion 11H which is positioned in the center in the width direction W, and a pair of less stretching portion 11L which are positioned on both sides in the width direction W and stretch less than the highly stretching portion 11H. The highly stretching portion 11H is a portion in which the elastic member 11 is attached in a highly stretched state when being attached to the absorbent main body AB, and shrinks with the sheet in a natural state so as to be in a bellows shape and to form a number of wrinkles 11S. That is, the highly stretching portion 11H is relatively increased in the basis weight, and has a higher rigidity compared to the less stretching portion 11L. The supporting portion 5b is fixed to the highly stretching portion 11H by the heat welding portion 50 (the (longitudinal direction) heat welding portion 50a, the (width direction) heat welding portion 50b).

Figure 4:
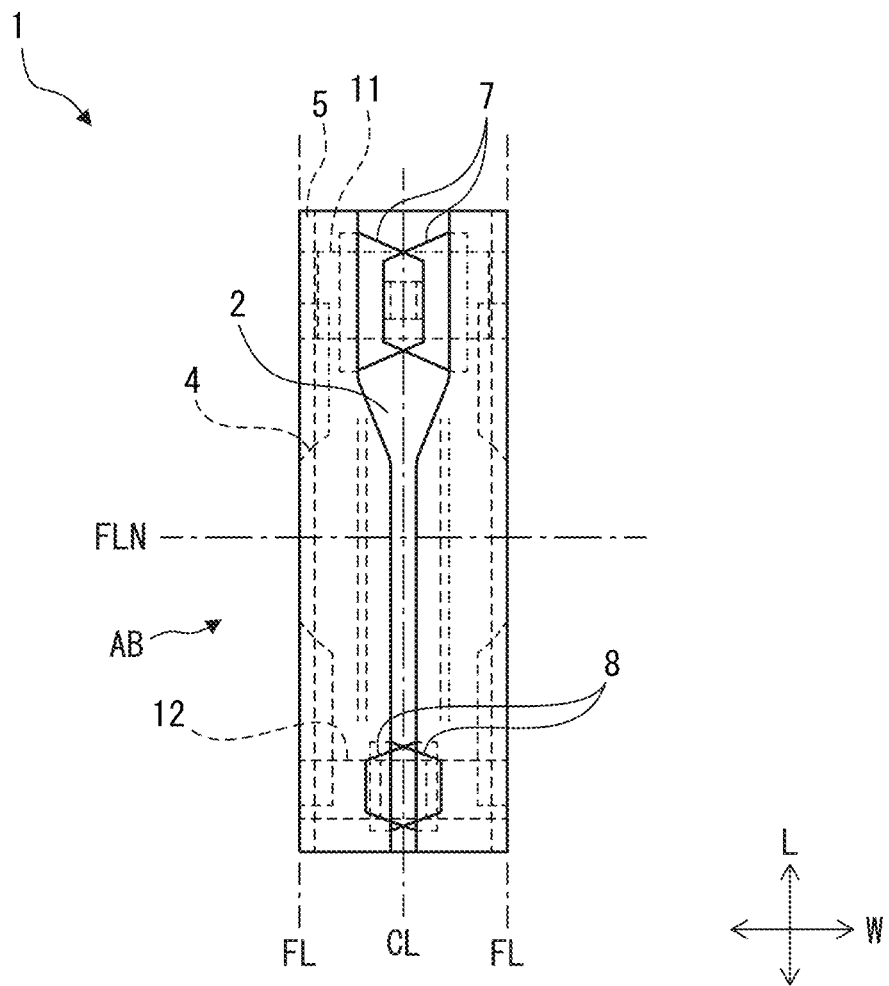
FIG. 4 is a view explaining a folding method of the absorbent article according to the first embodiment.
Figure 5:
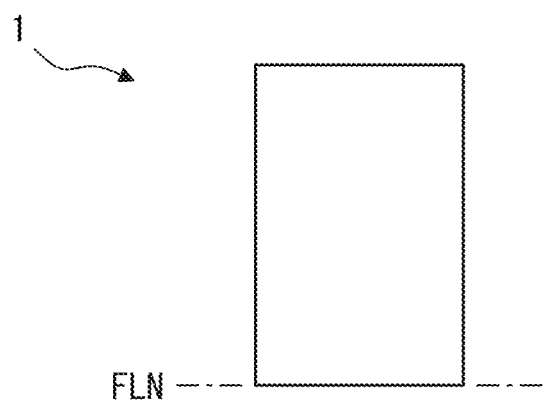
FIG. 5 is a view explaining the folding method of the absorbent article according to the first embodiment.

When the absorbent article 1 is packaged, the pair of side flaps 7, 7 are folded toward the inner side in the width direction, and further, the portion on the front side or the rear side of the absorbent main body AB is folded toward the rear side or the front side in the longitudinal direction L. One example of the specific folding method will be explained with reference to FIGS. 3 to 5. Note that FIGS. 4 and 5 are views explaining the folding method of the absorbent article 1 according to the present embodiment.

In the present embodiment, each of the pair of side flaps 7, 7 in the absorbent article 1 as shown in FIG. 3 is folded toward the inner side in the width direction W, at the position of the folding line FL which passes through the supporting portion 5b and extends along the longitudinal direction L in a plan view. When the absorbent article 1 is folded toward the inner side in the width direction W, at the position of the folding lines FL in this manner, the absorbent article 1 is to be in a shape shown in FIG. 4. Subsequently, the portion on the front side of the absorbent main body AB in the absorbent article 1 shown in FIG. 4 is folded toward the rear side in the longitudinal direction L at the position of the folding line FLN which overlaps with the central axis CW and extends along the width direction W, in a plan view. When the absorbent article 1 is further folded toward the rear side in the longitudinal direction L at the position of the folding line FLN in this manner, the absorbent article 1 is to be in a shape shown in FIG. 5. Subsequently, the folded absorbent article 1 as shown in FIG. 5 is packaged by a wrapping paper (which is not shown), so as to be a product. Incidentally, at this time, the position of the folding line FL may not overlap with the absorbent body 4 in the thickness direction T (or in a plan view), or may overlap with at least a portion of the absorbent body 4.

Next, the function obtained by the position of the folding line FL being provided at portions with rigidity will be explained. When the product is used, the package by the wrapping paper is opened, the folded absorbent article 1 is expanded, and used. At this time, there may be a case in which folding creases are formed by the folding of the absorbent article 1. As the portions in which the folding creases are easily formed, the portions close to the end portion on the dorsal side in the longitudinal direction L in the absorbent main body AB may be mentioned. The reason why the folding creases are formed is that such portion does not include the absorbent body 4 in the thickness direction T, and is formed mainly by thin materials, such as the top sheet 2, the back sheet 3, (or the exterior sheet 9), etc. FIG.

Figure 6A:
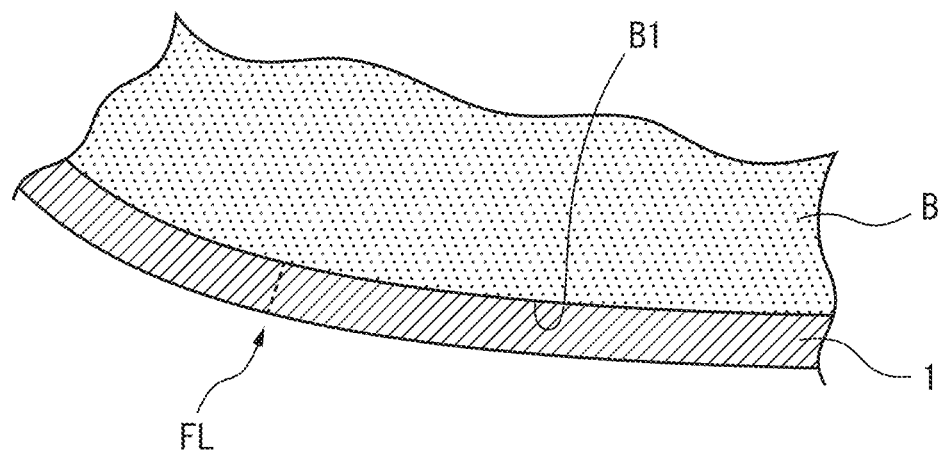
FIG. 6A and FIG. 6B are schematic views for explaining a function of the absorbent article according to the first embodiment.
Figure 6B:
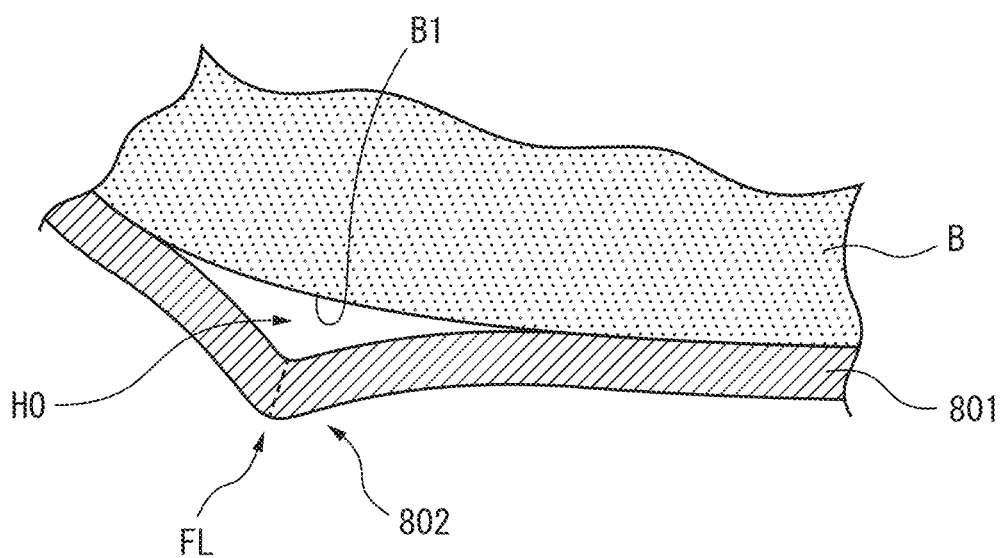

6A and FIG. 6B are schematic views explaining the function of the absorbent article according to the present embodiment, and FIG. 6A shows the case in which the folding creases are not present in the absorbent article 1, and FIG. 6B shows the case in which the folding creases are present in the absorbent article 1.

As shown in FIG. 6B, in a case in which the folding crease 802 is formed at the position of the folding line FL in the absorbent article 801, for example, at the position of the folding line FL in the region on the dorsal side in the longitudinal direction L, the portion at which the folding crease 802 is present is separated from the skin surface B1 of the body B of the wearer due to the shape of the folding crease 802, whereby there may be a case in which the gap H0 is formed in between the absorbent article 801 and the skin surface B1. Accordingly, there may be a case in which the excrement leaks out to the dorsal side, and the odor of the excrement leaks out to the dorsal side through the gap H0.

Accordingly, in the present embodiment, when the absorbent article 1 is folded, the position of the folding lines FL at which the pair of side flaps 7, 7 are folded and the supporting portion 5b are to overlap with each other in the thickness direction T (or in a plan view), in the above described manner. The supporting portion 5b is a portion of each of the leakage barriers 5, is fixed to the absorbent main body AB by the heat welding portion 50 (the heat welding portions 50a, 50b), and is overlapped with the elastic member 11. Accordingly, in the present embodiment, the position of the folding lines FL is provided at the portion in which the supporting portion 5b including the heat welding portion 50, the elastic member 11 and the absorbent main body AB are overlapped with each other, that is, the portion with rigidity. Consequently, the pair of side flaps 7, 7 of the absorbent article 1 are folded at the position of the folding lines FL at respective portions with rigidity, whereby when the absorbent article 1 is expanded, the folding creases can be suppressed from being formed at the position of the folding lines FL. Since the folding creases can be suppressed from being formed in the absorbent article 1, the region on the dorsal side in the longitudinal direction L of the absorbent article 1 can be made to curve along the skin surface B1 of the body B of the wearer, and is to be in close contact with the skin surface B1, as shown in FIG. 6A. That is, when the absorbent article 1 is worn, the gap between the absorbent article 1 and the skin surface B1 can be suppressed from being formed. As a result, excrement, for example, urine can be prevented from leaking out to the dorsal side, and the odor of the excrement can be prevented from leaking out to the dorsal side.

In the preferable mode of the present embodiment, the heat welding portion 50 of the supporting portion 5b has the predetermined widths on both sides of the folding line FL. That is, the heat welding portion 50 is formed so as to stride over the folding line FL. Accordingly, even when the folding lines FL along the longitudinal direction L are shifted in the width direction W to some extent, the folding lines FL can more reliably pass through the heat welding portion 50. That is, the folding lines FL can more reliably pass through the portions with rigidity, whereby the folding creases can be even more suppressed from being formed at the position of the folding lines FL. Accordingly, the gap between the absorbent article 1 and the skin surface can be even more suppressed from being formed.

Further, in the preferable mode of the present embodiment, the heat welding portion 50 of the supporting portion 5b is continuously or intermittently formed from one end portion to the other end portion in the longitudinal direction L of the supporting portion 5b, whereby the rigidity of the supporting portion 5b through which the folding lines FL pass can be even more increased, and the folding creases can be even more suppressed from being formed at the position of the folding lines FL. Accordingly, the gap between the absorbent article 1 and the skin surface can be even more suppressed from being formed.

Further, in the preferable mode of the present embodiment, the position of the folding lines FL and the highly stretching portion 11H in the elastic member 11 are overlapped with each other in the thickness direction T. The highly stretching portion 11H is a portion in which the elastic member 11 is attached in a highly stretched state when being attached to the back sheet 3 of the absorbent main body AB, and shrinks with the back sheet 3 in a natural state so as to be in a bellows shape and to form a number of wrinkles. That is, the highly stretching portion 11H is relatively increased in the basis weight, and has a higher rigidity compared to the less stretching portion 11L. Accordingly, the position of the folding lines FL is provided at such portions with rigidity. Consequently, by folding the pair of side flaps 7, 7 of the absorbent article 1 at the position of the folding lines FL at respective portions with rigidity, the folded portions can easily transition from the folded state to the expanded state when being worn, whereby the gap between the absorbent article 1 and the skin surface B1 can be suppressed from being formed. Accordingly, the leakage of the excrement to the dorsal side and the tendency of the odor of the excrement being easily leaked to the dorsal side can be prevented.

Further, in the preferable mode of the present embodiment, the position of the folding lines FL and at least a portion of the absorbent body 4 are overlapped with each other in the thickness direction T. The absorbent body 4 is somewhat separated from the end portion in the longitudinal direction L in the dorsal side region of the absorbent main body AB, however, by the absorbent body 4 also being bent when the side flaps 7 are folded, the bending of the end portion in the longitudinal direction L in the dorsal side region of the absorbent main body AB, in which the folding creases are easily formed, can be moderate. Accordingly, the suppression of the folding creases by making the folding lines FL pass through the supporting portion can be assisted. Consequently, the gap between the absorbent article 1 and the skin surface can be suppressed from being formed. Accordingly, the leakage of the excrement to the dorsal side and the tendency of the odor of the excrement being easily leaked to the dorsal side can be prevented.

Further, in the preferable mode of the present embodiment, the position of the folding lines FL, the other region in the longitudinal direction L in the absorbent main body AB, that is, the ventral side region, and the joining target member 12 are overlapped with each other in the thickness direction T. That is, the position of the folding lines FL is provided at portions with rigidity. Consequently, by folding the pair of side flaps 7, 7 of the absorbent article 1 at the position of the folding lines at respective portions with rigidity, the folded portions can easily transition from the folded state to the expanded state when being worn, whereby the gap between the absorbent article 1 and the skin surface can be suppressed from being formed. Accordingly, the leakage of the excrement to the dorsal side and the tendency of the odor of the excrement being easily leaked to the dorsal side can be prevented.

Figure 7:
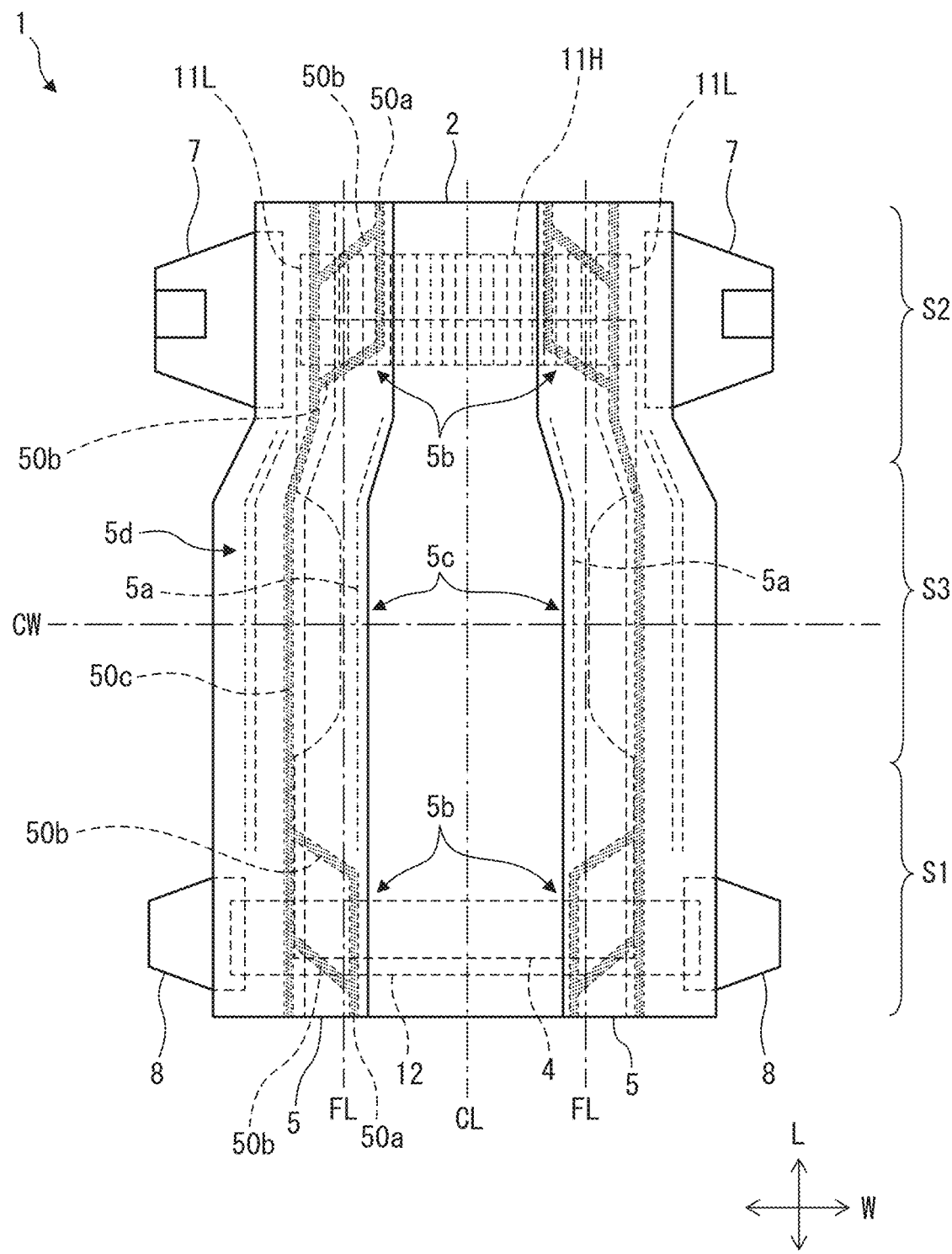
FIG. 7 is a view showing another state of the absorbent article according to the first embodiment.

Incidentally, when the absorbent article 1 which is in a state of being expanded as shown in FIG. 3 is put back to a natural state in the width direction W, that is, when the elastic member 11 is released from the state of being stretched toward the outer side in the width direction W so as to be put back to a natural state, the length in the width direction W mainly in the dorsal side waist region S2 decreases. FIG. 7 is a view showing another state of the absorbent article according to the present embodiment. That is, as shown in FIG. 7, by the shrinkage of the elastic member 11, the length in the width direction W of the dorsal side waist region S2 is to be shorter compared to that in a case of the absorbent article 1 of FIG. 3. In the present embodiment, as shown in FIG. 7, even in a case of the absorbent article 1 in which the length in the width direction W in the dorsal side waist region S2 is relatively short, when the absorbent article 1 is folded, the position of the folding lines FL at which the pair of side flaps 7, 7 are folded and the supporting portion 5*b* can be made to overlap with each other in the thickness direction T (or in a plan view). That is, the position of the folding lines FL can be provided at the portion in which the supporting portion 5*b* including the heat welding portion 50, the elastic member 11 and the absorbent main body AB are overlapped with each other, that is, the portion with rigidity. Accordingly, also in this case, the functions and effects which are the same as those in the above mentioned case shown in FIG. 3 can be obtained.

Note that, in the present embodiment, the heat welding portion 50 indicates the portion in which the leakage barriers 5 and the top sheet 2 are melted by heat so as to be joined to each other, however, the heat welding portion 50 may also be the portion in which the leakage barriers 5, the top sheet 2 and the elastic member 11 are melted by heat so as to be joined to each other.

Figure 8A:
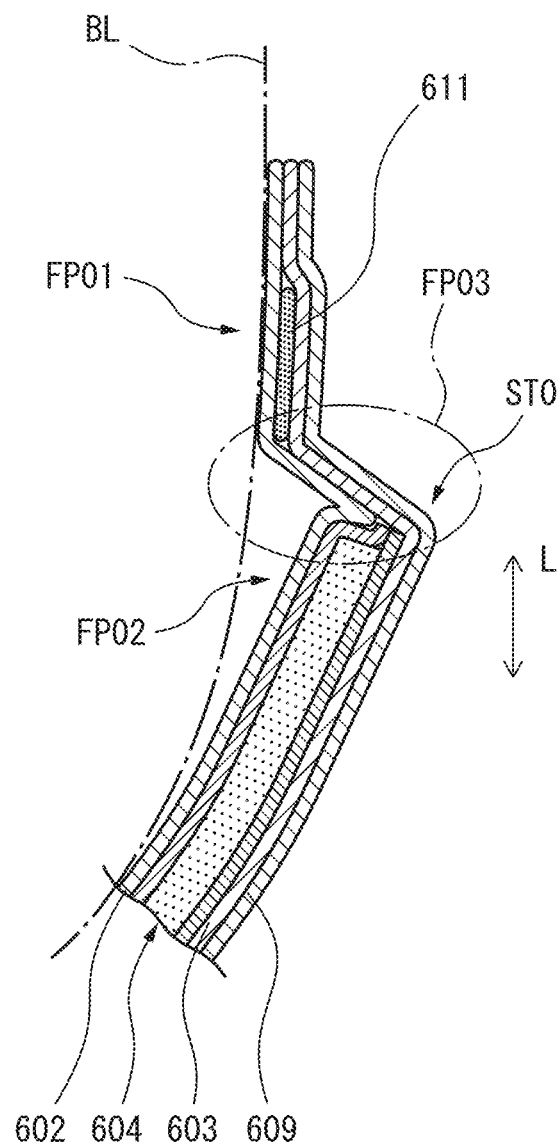
FIG. 8A and FIG. 8B are schematic views for explaining a function of the absorbent article according to the first embodiment.
Figure 8B:
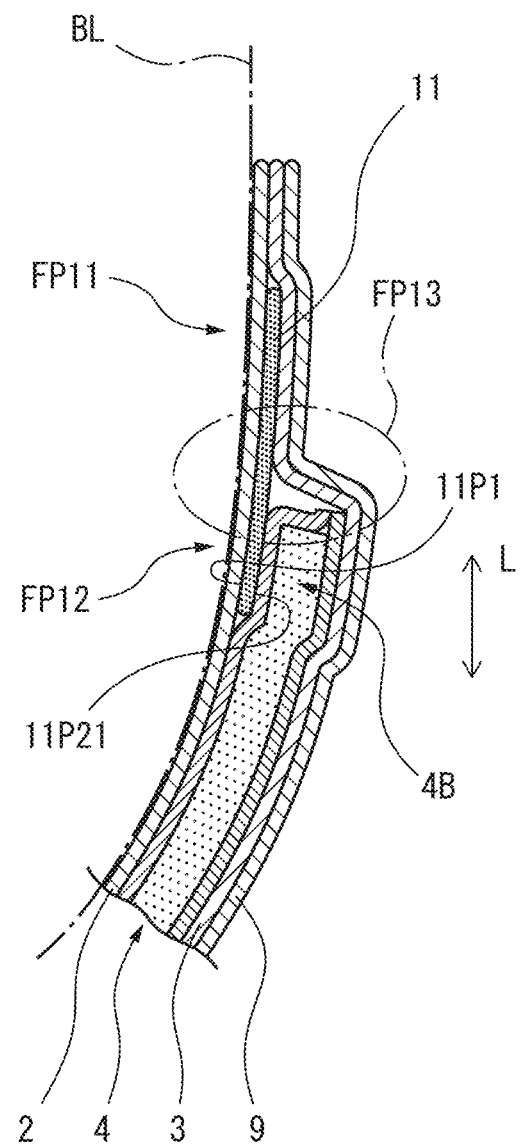

Next, another function of the absorbent article 1 will be explained with reference to FIG. 8A and FIG. 8B. FIG. 8A and FIG. 8B are schematic views which explains another function of the absorbent article 1. FIG. 8A shows a general absorbent article, and FIG. 8B shows the absorbent article 1 of the present embodiment. In the absorbent article shown in FIG. 8A, the elastic member 611 on the dorsal side is disposed in between the top sheet 602 and the back sheet 603, is not overlapped with the absorbent body 604 in the thickness direction, and thus is not joined to the absorbent body 604. In other words, in the laminated body of the top sheet 602 and the back sheet 603, the elastic member 611 and the absorbent body 604 are separated in the longitudinal direction L. In this case, when the elastic member 611 shrinks and approaches the dorsal surface BL of the wearer so as to be in close contact with the dorsal surface BL of the wearer, the portion FP01 of the top sheet 602 which corresponds to the elastic member 611 can be in close contact with the dorsal surface BL of the wearer.

However, since the absorbent body 604 does not have a stretching and shrinking property and does not shrink, and is separated from the elastic member 611, whereby the absorbent body 604 cannot follow the movement of the elastic member 611, the absorbent body 604 on the contrary is to be separated from the dorsal surface BL of the wearer. Accordingly, the portion FP02 of the top sheet 602 which corresponds to the absorbent body 604 is to be separated from the dorsal surface BL of the wearer. In addition, since the top sheet 602 and the back sheet 603, which are positioned in between the absorbent body 604 and the elastic member 611, also do not have a stretching and shrinking property and do not shrink, do not overlap with the elastic member 611 in the thickness direction, and are not joined thereto, whereby the top sheet 602 and the back sheet 603 cannot follow the movement of the elastic member 611, the top sheet 602 and the back sheet 603 are to be separated from the dorsal surface BL of the wearer. Accordingly, the portion FP03 of the top sheet 602 in between the absorbent body 604 and the elastic member 611 also is to be separated from the dorsal surface BL of the wearer. As a result, the level difference ST0 is formed in between the elastic member 611 and the absorbent body 604 on the dorsal surface side of the wearer. When such level difference ST0 is formed, the fitting property to the body of the wearer is substantially decreased, whereby there may be a case in which the wearing comfortability of the absorbent article is decreased, and the portion in the absorbent body 604 on the dorsal side of the wearer cannot sufficiently absorb excretory fluid.

In order to suppress such level difference ST0 from being formed, in the absorbent article 1, by the above mentioned configuration as shown in FIGS. 1 and 2 in which the elastic member 11 and the pair of side flaps 7, 7 are applied, the fitting property to the body of the wearer can be improved, and the decrease in the absorption property of the absorbent body and the decrease in the wearing comfortability can be suppressed. To be more specific, the configuration will be described as follows.

As shown in FIG. 8B, the elastic member 11 and the absorbent body 4 are overlapped and are in contact with each other in the thickness direction T, however, since the absorbent body 4 does not intervene in between the elastic member 11 and the top sheet 2, the function of the elastic member 11 being pressed toward the skin side works directly to the top sheet 2 on the skin side, and is not weakened by the absorbent body 4. Accordingly, the fitting property to the body of the wearer of the absorbent article 1 by the elastic member 11 can be improved. Further, the elastic member 11 and the absorbent body 4 are overlapped and are in contact with each other in the thickness direction T, and the non-skin side surface 11*p*21 of the elastic member 11 is in contact with the absorbent body 4, however, the elastic member 11 and the absorbent body 4 are not joined to each other, and accordingly, are not adhered for example by an adhesive agent, etc. In these manners, since the elastic member 11 and the absorbent body 4 are not joined to each other, and are not adhered by an adhesive agent, etc., the elastic member 11 and the absorbent body 4 are not so much influenced by the movement thereof from each other. That is, the elastic member 11 and the absorbent body 4 are capable of relatively and mutually moving from each other. Accordingly, the elastic member 11 can shrink without receiving influence of the absorbent body 4. At this time, since the elastic member 11 is positioned close to the end portion on the dorsal side in the longitudinal direction L in the absorbent main body AB, in which the folding creases are easily formed, the elastic member 11 can shrink even more easily when the absorbent article 1 is worn, whereby the folding creases can be suppressed, and the gap between the absorbent article 1 and the skin surface can be suppressed from being formed.

On the other hand, in a case in which the elastic member 11 is shrunk in the width direction W so as to improve the fitting property to the body of the wearer, the absorbent body 4 hardly shrinks, and accordingly, the deformation of the absorbent body 4 hardly occurs, whereby the decrease in the absorption property of the absorbent body 4 and the decrease in the wearing comfortability of the absorbent body 4 can be suppressed. As a result, since the absorbent body 4 can be in even closer contact with the wearer, the absorption property can be improved, and the fitting property to the body of the wearer can be improved. However, since the elastic member 11 and the absorbent body 4 are not joined to each other, when the elastic member 11 is pressed toward the skin side, the absorbent body 4 tends to be separated from the elastic member 11, whereby pushing out of the absorbent body 4 toward the skin side may be weaker. However, in the present embodiment, the rear side portion 11b in the elastic member 11 which does not overlap with the absorbent body 4 in the thickness direction T is joined to the back sheet 3. Accordingly, when the elastic member 11 is pressed toward the skin side, the absorbent body 4 can be pressed toward the skin side by the back sheet 3 which is on the further non-skin side than the absorbent body 4, whereby it can be difficult for the absorbent body 4 to be separated from the skin. Further, in the present embodiment, in the both end portions in the width direction W of the front side portion 11a, the skin side surface is joined to the top sheet 2 and the non-skin side surface is joined to the back sheet 3. Accordingly, when the absorbent article 1 is worn, the elastic member 11 is stretched in the width direction W, whereby the laminated body of the back sheet 3 and the top sheet 2 can be stretched in the width direction W, and accordingly the absorbent body 4 in the laminated body can be stretched in the width direction W, so that the absorbent body 4 can be easily fitted to the skin. Still further, in the present embodiment, the shrinking force of each of the pair of side flaps 7, 7 works in the both end portions in the width direction W of the laminated body of the top sheet 2 and the back sheet 3, and accordingly, by the laminated body, and especially the back sheet 3 being pulled by the pair of side flaps 7, 7, the end portion in the width direction W of the absorbent body 4 is pressed toward the skin side by the back sheet 3, whereby the pushing out of the absorbent body 4 toward the skin side is suppressed from being weaker, and from being separated from the skin surface. Accordingly, the absorbent body 4 can be in close contact with the skin side with the elastic member 11.

As mentioned above in the present embodiment, while maintaining close contact between the absorbent body 4 and the skin surface by the top sheet 2, the back sheet 3 and the pair of side flaps 7, 7, the elastic member 11 is disposed on the skin side than the absorbent body 4, the absorbent body 4 and the elastic member 11 are not joined with each other, and thereby the shrinkage of the elastic member 11 is made easier. Accordingly, by the shrinkage of the elastic member 11 when the absorbent article 1 is worn, the folding creases of the absorbent article 1 can be suppressed, and the gap between the absorbent article 1 and the skin surface can be suppressed from being formed.

Figure 9:
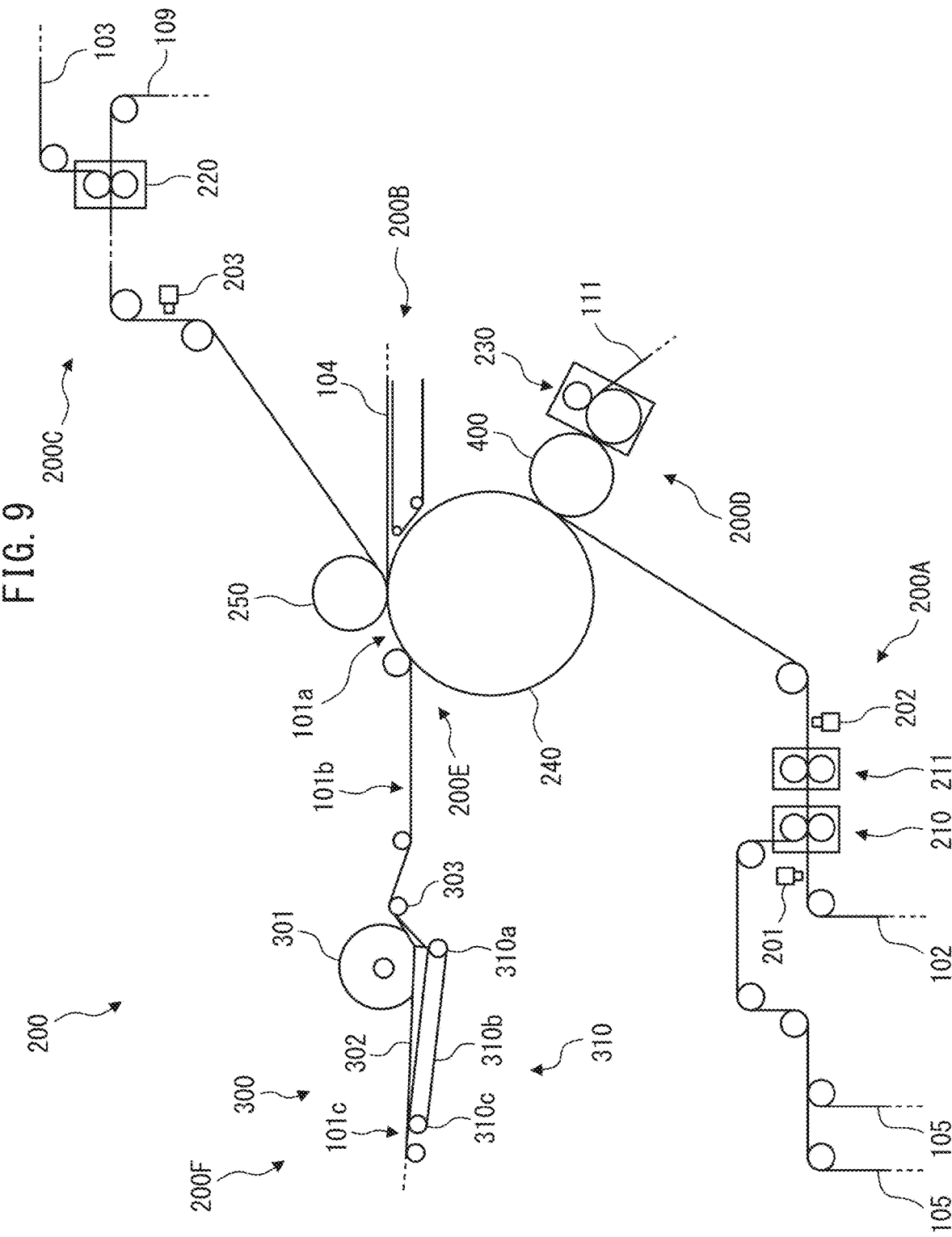
FIG. 9 is a schematic entire view of a manufacturing apparatus of the absorbent article according to the first embodiment.

Next, the manufacturing method of the absorbent article according to the present embodiment will be explained. FIG. 9 shows an example of a configuration of a manufacturing apparatus 200 of the absorbent article 1 according to the present embodiment. The manufacturing apparatus 200 includes a top sheet forming unit 200A, an absorbent body forming unit 200B, a back sheet forming unit 200C, an elastic member joining unit 200D, an integration joining unit 200E, and a folding unit 200F. Further, the manufacturing method of the absorbent article which uses the manufacturing apparatus 200 includes a top sheet forming step, an elastic member joining step, an absorbent body forming step, a back sheet forming step, an integration joining step, a shrinking step, a pressing step, and a folding step.

Regarding the conveyance of the absorbent article 1 and the materials which configure the absorbent article 1, etc., the manufacturing apparatus 200 includes a machine direction MD, a cross machine direction CD which is orthogonal to the machine direction MD and is along the conveyance surface, and a transverse direction TD which is orthogonal to the machine direction MD and to the cross machine direction CD. Note that the longitudinal direction, the width direction, and the thickness direction of the absorbent article 1 and the materials which configure the absorbent article 1 are respectively the same as the machine direction MD, the cross machine direction CD, and the transverse direction TD. Accordingly, in the absorbent article 1 and the materials which configure the absorbent article 1, the longitudinal direction, the width direction, and the thickness direction are hereinbelow referred to as the machine direction MD, the cross machine direction CD, and the transverse direction TD.

In the top sheet forming step, a continuous top sheet 102 to which continuous leakage barrier sheets 105, 105 are joined is formed, by the top sheet forming unit 200A. Specifically, the continuous top sheet 102 which is the continuous sheet for the top sheet 2 is applied with an adhesive agent on one surface by an adhesive agent applying device 201 while being conveyed by a plurality of conveyance rolls, and is supplied to joining rolls 210. Meanwhile, the pair of continuous leakage barrier sheets 105, 105 which are the continuous sheets for the pair of leakage barrier are conveyed by a plurality of conveyance rolls to be supplied to the joining rolls 210. Accordingly, in the joining rolls 210, the continuous top sheet 102 and the pair of continuous leakage barrier sheets 105, 105 are supplied in between the pair of joining rolls which are disposed in a state of facing each other. Subsequently, the pair of continuous leakage barrier sheets 105, 105 are pressed onto the surface of the continuous top sheet 102 to which the adhesive agent is applied and are adhered thereto, whereby the continuous top sheet 102, in which the pair of continuous leakage barrier sheets 105, 105 are joined on both sides in the cross machine direction CD is formed. Subsequently, the continuous top sheet 102 to which the pair of continuous leakage barrier sheets 105, 105 are joined is supplied in between a pair of heat rolls of heat rolls 211 which are disposed in a state of facing each other, and heated to be heat-welded. In this case, a predetermined pattern is formed on the heat rolls so that the heat welding portion (the heat welding portion 50 of the absorbent article 1) with a predetermined pattern is formed on the pair of continuous leakage barrier sheets 105, 105, and the heating and the heat welding are performed at the predetermined pattern. Subsequently, the continuous top sheet 102 is applied with an adhesive agent by an adhesive agent applying device 202 on the other surface thereof which is the opposite side of the surface to which the continuous leakage barrier sheets 105, 105 are joined, while being conveyed by the plurality of conveyance rolls, followed by being supplied to the integration joining unit 200E (the joining roll 240).

In the elastic member joining step, the continuous top sheet 102 to which the elastic member 11 is adhered is formed by the elastic member joining unit 200D. Specifically, a continuous elastic member sheet 111 which is a continuous sheet for the elastic member 11 is supplied to a cutting device 230 while being conveyed by the plurality of conveyance rolls, and a tip portion in the machine direction MD is cut to a predetermined length by a cutter (a cutting machine) of the cutting device 230. The both end portions in the cross machine direction CD of the cutting piece which is the elastic member 11 are received by a width widening adhering device 400 and are retained by the width widening adhering device 400. The elastic member 11 is rotated by approximately 180° while the both end portions in the cross machine direction CD are stretched in the cross machine direction by the width widening adhering device 400, is pressed in a stretched state onto the adhesive agent applied surface of the continuous top sheet 102 on a joining roll 240 after the top sheet forming step, and is adhered to the continuous top sheet 102. Accordingly, the continuous top sheet 102 to which the elastic member 11 is adhered is formed. The both end portions themselves in the elastic member 11 which are held by the width widening adhering device 400 are hardly stretched, whereby are the less stretching portion, and the center portion thereof which is not held by the width widening adhering device 400 is strongly stretched, whereby is the highly stretching portion. At this time, the continuous top sheet 102 is applied with a tension force in the machine direction, and even when the elastic member 11 which is in a stretched state of being stretched in the cross machine direction CD is adhered thereto, the continuous top sheet 102 hardly decreases the width thereof. Subsequently, the continuous top sheet 102 to which the elastic member 11 is adhered moves to the integration joining unit 200E (the joining roll 250) above the joining roll 240, and is supplied to the integration joining unit 200E (the joining roll 240). At this time, the elastic member 11 is adhered on the surface to which the adhesive agent is applied in the continuous top sheet 102, the adhesive agent is not present on the elastic member 11, and the adhesive agent is in a state of being applied around the elastic member 11.

In the absorbent body forming step, an absorbent body 104 is formed by an absorbent body forming device which is not shown in the absorbent body forming unit 200B. Subsequently, the absorbent body 104 is supplied to the integration joining unit 200E (the joining rolls 240, 250) by a conveyance belt.

In the back sheet forming step, a continuous back sheet 103 to which a continuous exterior sheet 109 is joined is formed, by the back sheet forming unit 200C. Specifically, the continuous back sheet 103 which is a continuous sheet for the back sheet 3 is conveyed by a plurality of conveyance rolls and is supplied to a joining rolls 220. Meanwhile, the continuous exterior sheet 109 which is a continuous sheet for the exterior sheet 9 (which has been added with the leg portion elastic member 6, the side flaps 7, the protruded portion 8, and the joining target member 12) is applied with an adhesive agent on one surface by an adhesive agent applying device while being conveyed by a plurality of conveyance rolls, and is supplied to the joining rolls 220. In the joining rolls 220, the continuous exterior sheet 109 and the continuous back sheet 103 are supplied in between a pair of joining rolls which are disposed in a state of facing each other. Further, the continuous back sheet 103 is pressed onto the surface of the continuous exterior sheet 109 to which the adhesive agent is applied and is adhered thereto, whereby the continuous back sheet 103 to which the continuous exterior sheet 109 is joined on the back surface side is formed. Subsequently, the continuous back sheet 103 is applied with an adhesive agent by the adhesive agent applying device 203 on the other surface thereof which is the opposite side of the surface to which the continuous exterior sheet 109 is joined, while being conveyed by the plurality of conveyance rolls, followed by being supplied to the integration joining unit 200E (the joining rolls 240, 250).

In the integration joining step, a semi-product continuous body 101a for the absorbent article that includes the continuous top sheet 102, the absorbent body 104, and the continuous back sheet 103 is formed, by the integration joining unit 200E. Specifically, from the elastic member joining step, the continuous top sheet 102 to which the continuous leakage barrier sheets 105, 105 are joined, the adhesive agent is applied and the elastic member 11 is adhered; from the absorbent body forming step, the absorbent body 104; and from the back sheet forming step, the continuous back sheet 103 to which the continuous exterior sheet 109 is joined and the adhesive agent is applied, are respectively conveyed in between the joining rolls 240, 250 which are disposed in a state of facing each other. Subsequently, the continuous top sheet 102, the absorbent body 104, and the continuous back sheet 103 are sandwiched and compressed in between the pair of joining rolls 240, 250, so as to be joined. Accordingly, the semi-product continuous body 101a of the absorbent article that includes the continuous top sheet 102, the absorbent body 104, and the continuous back sheet 103 is formed. At this time, in the continuous top sheet 102 to which the elastic member 11 is adhered, the adhesive agent is not applied on the elastic member 11, whereby the adhesive agent is not present in between the elastic member 11 and the absorbent body 104, and accordingly, the elastic member 11 and the absorbent body 104 are in contact with each other, however, are not joined to each other. Incidentally, the application pattern of the adhesive agent to the top sheet 2, and application pattern of the adhesive agent to the back sheet 3 may for example be suitably adjusted by the adhesive agent applying device 202 and the adhesive agent applying device 203. For example, one piece of the absorbent article among the semi-product continuous body 101a may be the absorbent article 1 as shown in FIG. 3.

In the shrinking step, the semi-product continuous body 101a is separated from the joining roll 240, and is decreased with the tension force in the machine direction MD, while being conveyed by the plurality of conveyance rolls (for example, by decreasing the rotation number of the conveyance rolls). Accordingly, the elastic member 11 which is in a state of being stretched in the cross machine direction CD is to be shrinkable, whereby the elastic member 11 can be shrunk in the cross machine direction CD. In accordance thereto, the portion of a semi-product 1a which includes the elastic member 11 can also be shrunk in the cross machine direction CD. As a result, a semi-product continuous body 101b in which the portion including the elastic member 11 is shrunk in the cross machine direction CD, is formed. For example, one piece of the absorbent article among the semi-product continuous body 101b may be the absorbent article 1 as shown in FIG. 7.

Subsequently, in the pressing step, the semi-product continuous body 101b in which the elastic member 11 is shrunk, is supplied to a pressing member 301 and a conveyance device 310, by the conveyance roll 303 of the folding unit 200F. Subsequently, the central region in the cross machine direction CD of a semi-product 1b is pressed to the direction toward the placement surface of the semi-product 1b, by the pressing member 301 in which the length in the cross machine direction CD is shorter than the length in the cross machine direction CD of the elastic member 11, while the semi-product continuous body 101b is conveyed in the machine direction MD by the conveyance device 310. Accordingly, the region in which the plurality of wrinkles are present of the elastic member 11 is pressed.

In the folding step, a pair of side portion regions on the outer side in the cross machine direction CD than the central region in the semi-product 1b are held upward to the direction opposite to the direction toward the placement surface of the semi-product 1b and are respectively folded over the central region, at the positions of the pair of folding lines which extend along the machine direction MD, by the folding member 302, while the semi-product continuous body 101b is conveyed in the machine direction MD by the conveyance device 310. Accordingly, the semi-product continuous body 101c is formed. One piece of the absorbent article among the semi-product continuous body 101c may be the absorbent article 1 as shown in FIG. 4. Incidentally, the pressing step and the folding step may be performed in a temporally overlapping manner, or the folding step may be performed after the pressing step. The semi-product continuous body 101c is subsequently separated, for example, into one piece of the absorbent article, and further folded (into the absorbent article 1 as shown in FIG. 5) so as to be packaged as the absorbent article 1.

In the above mentioned manner, the absorbent article 1 is manufactured.

According to the present absorbent article 1, the gap H0 between the absorbent main body AB and the skin surface B1 can be suppressed from being formed when being worn.

Further, as the preferable mode of the absorbent article according to the present embodiment, in the longitudinal direction L, the elastic member 11 is shifted toward the rear side direction in the longitudinal direction L than the absorbent body 4. Accordingly, the friction, etc., between the elastic member 11 and the absorbent body 4 is decreased compared to a case in which the elastic member 11 and the absorbent body 4 are completely overlapped with each other in the thickness direction T, whereby the elastic member 11 can even more easily stretch and shrink in the width direction W. Consequently, by the shrinkage of the elastic member 11, the wrinkles 11S in the highly stretching portion 11H are increased, that is, the basis weight is relatively increased, whereby the rigidity can be even more increased. Accordingly, when the pair of side flaps 7, 7 are folded, the pair of side flaps 7, 7 can be folded at portions with more rigidity, and the folding creases can be suppressed from being formed at the portion of the folding lines.

In another preferable embodiment of the present absorbent article, the adhesive agent is not disposed also in the outer side peripheral of the region in which elastic member 11 and the absorbent body 4 are overlapped with each other, in a plan view. Accordingly, the elastic member 11 and the absorbent body 4 are capable of relatively and mutually moving from each other. Accordingly, the elastic member 11 can shrink without receiving influence of the absorbent body 4, and the rigidity can be even more increased. Accordingly, when the pair of side flaps 7, 7 are folded, the pair of side flaps 7, 7 can be folded at portions with more rigidity, and the folding creases can be suppressed from being formed at the portion of the folding lines.

Second Embodiment

Figure 10A:
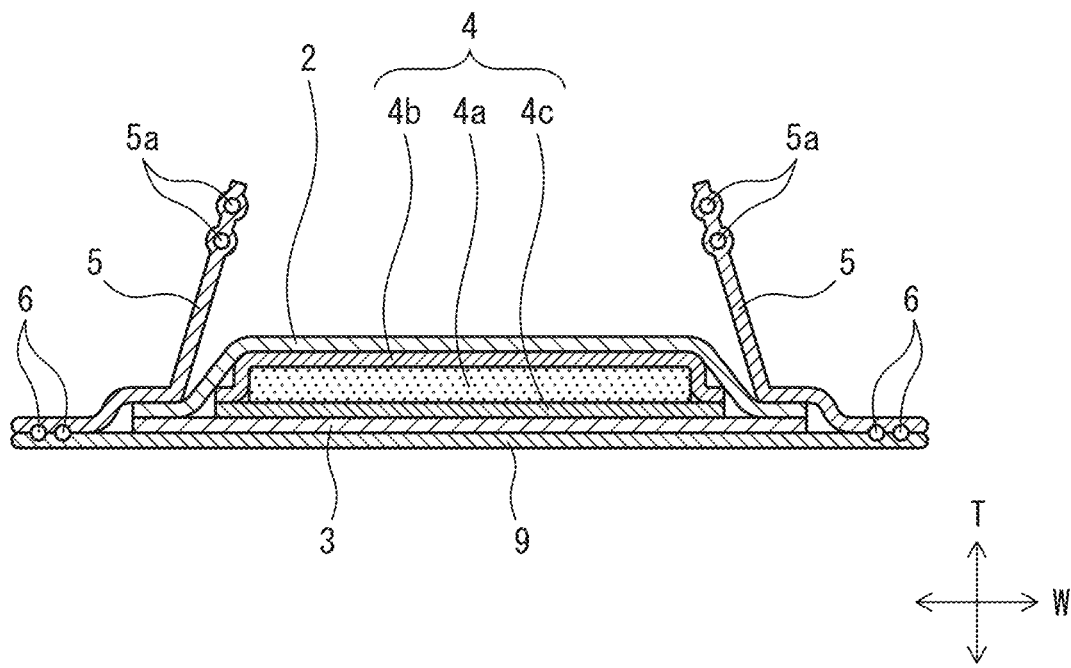
FIG. 10A and FIG. 10B are views showing an absorbent article according to a second embodiment.
Figure 10B:
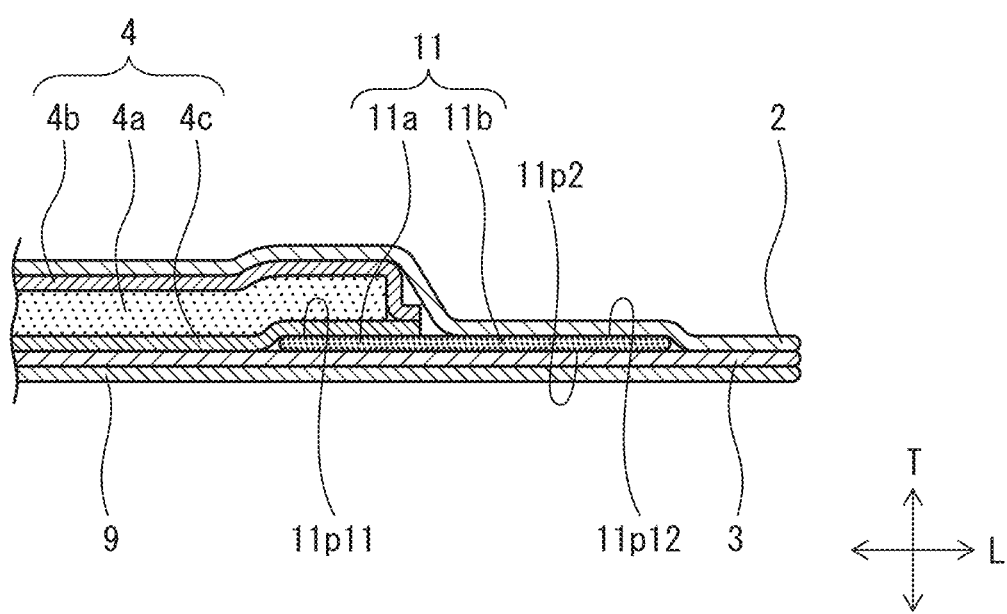

Next, the second embodiment will be explained. The present embodiment is different from the embodiment in which the elastic member 11 is positioned on the skin surface side with respect to the absorbent body 4 or the top sheet 2 side, in that the elastic member 11 is positioned on the non-skin surface side with respect to the absorbent body 4 or the back sheet 3 side. Hereinbelow, the differences will be mainly explained. FIG. 10A and FIG. 10B are views showing the absorbent article according to the present embodiment, and FIG. 10A is a sectional view along the line IIa-IIa' shown in FIG. 1, and FIG. 10B is a sectional view along the line IIb-IIb' shown in FIG. 1.

First, the differences in the configuration of the absorbent article 1 according to the present embodiment will be explained. In the present embodiment, the front side portion 11a in the elastic member 11 is a portion on the front side in the longitudinal direction L, overlaps with the absorbent body 4 in the thickness direction T (except for the both end portions in the width direction W), and is positioned closer to the non-skin side than the absorbent body 4. On the other hand, the rear side portion 11b is a portion on the rear side in the longitudinal direction L, which does not overlap with the absorbent body 4 in the thickness direction T, and overlaps with the top sheet 2. In the elastic member 11, the skin side surface 11p11 of the front side portion 11a is in contact with the absorbent body 4, and is adhered thereto by an adhesive agent, etc. On the other hand, the skin side surface 11p12 of the rear side portion 11b is not in contact with the absorbent body 4, however, is in contact with the top sheet 2, and is adhered thereto by an adhesive agent, etc. Further, the non-skin side surface 11p2 of the front side portion 11a and the rear side portion 11b is in contact with the back sheet 3, and is adhered thereto by an adhesive agent, etc. The absorbent body 4 is in contact with the top sheet 2, and is joined thereto by an adhesive agent, etc. Accordingly, the elastic member 11, the top sheet 2, and the absorbent body 4 overlap with each other in the thickness direction T, and are joined by an adhesive agent, etc. Consequently, the front side portion 11a of the elastic member 11 is not directly joined to the top sheet 2, however, by the stretching and shrinking of the elastic member 11, the top sheet 2 shrinks, whereby the leakage barriers 5 can also follow the movement of the elastic member 11, through the heat welding portions 50a, 50b.

Figure 11:
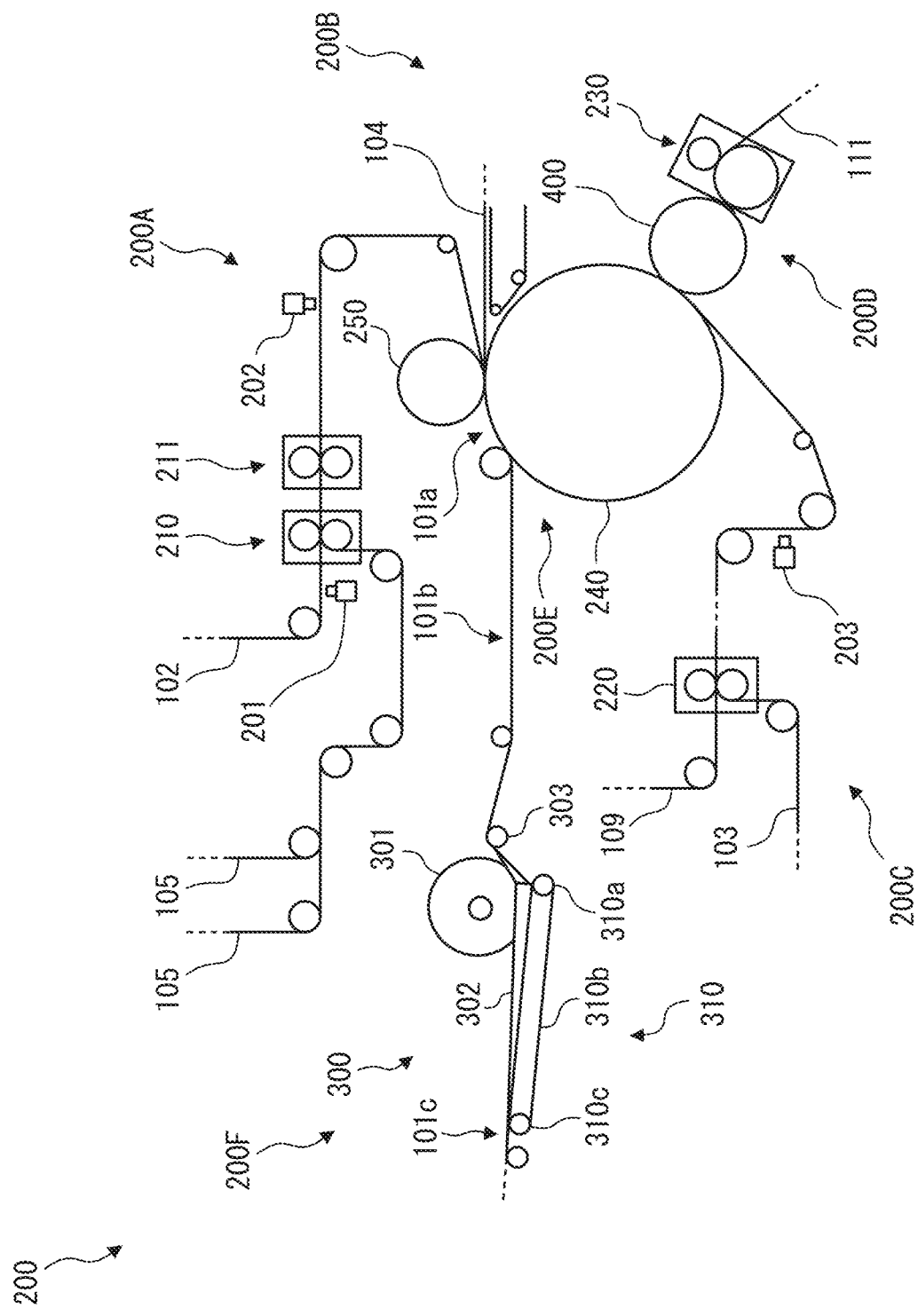
FIG. 11 is a schematic entire view of a manufacturing apparatus of the absorbent article according to the second embodiment.

Next, the differences in the manufacturing method of the absorbent article 1 according to the present embodiment will be explained. FIG. 11 shows the example of the configuration of the manufacturing apparatus 200 of the absorbent article 1 according to the present embodiment. The present embodiment is different from the first embodiment in which the elastic member joining unit 200D is disposed immediately after the top sheet forming unit 200A, in that in the manufacturing apparatus 200, the elastic member joining unit 200D is disposed immediately after the back sheet forming unit 200C. That is, the present embodiment is different from the first embodiment in which the elastic member joining step is performed immediately after the top sheet forming step and the elastic member 11 is adhered onto the continuous top sheet 102 (the top sheet 2), in that in the manufacturing method, the elastic member joining step is performed immediately after the back sheet forming step and the elastic member 11 is adhered onto the continuous back sheet 103 (the back sheet 3).

The present embodiment can achieve the functions and effects which are similar to those in the first embodiment. Further, since the elastic member 11 is present on the non-skin side than the absorbent body 4, and the absorbent body 4 can be pressed toward the skin side, the occurrence of the gap between the absorbent body 4 and the skin surface B1 can be suppressed. Still further, the top sheet 2 can be pressed toward the skin side through the absorbent body 4, whereby the degree of folding of the folding creases which are formed on the top sheet 2 can be decreased.

The absorbent article according to the present invention is not limited to the respective embodiments as described above, and combinations, modifications, etc., can appropriately be made within the scope without departing from the object and the purpose of the present invention.

The invention claimed is:

1. An absorbent article which includes a longitudinal direction, a width direction, and a thickness direction that are mutually orthogonal to each other, and has a dorsal side waist region, a crotch region, and a ventral side waist region, said absorbent article comprising:

an absorbent main body including a top sheet, a back sheet, and an absorbent body which is positioned in between the top sheet and the back sheet;

a pair of side flaps that extend to both outer sides in the width direction of the absorbent main body, in the dorsal side waist region; and a pair of leakage barriers that are disposed in the absorbent main body, wherein a direction toward and a direction away from a longitudinal direction central axis of the absorbent main body in the width direction are respectively an inner side direction and an outer side direction, the absorbent article further comprising:
an elastic member which is joined in between the pair of side flaps in the absorbent main body, and is stretchable and shrinkable in the width direction, wherein each of the pair of leakage barriers includes:
a standing portion in which an outer side in the width direction is a fixed end, and an inner side in the width direction is a free end, and
a supporting portion which is adjacent to one side in the longitudinal direction of the standing portion and overlaps with the elastic member in the thickness direction, the supporting portion is fixed to the absorbent main body by a heat welding portion, each of the pair of side flaps is folded to an inner side in the width direction at a position of a folding line which passes through the supporting portion and extends along the longitudinal direction in a plan view, the elastic member includes:
a first stretching portion which is positioned in a center in the width direction, and
a pair of second stretching portions which are positioned on both sides in the width direction and stretch less than the first stretching portion, the folding line overlaps with the first stretching portion in the thickness direction, at least a portion of the elastic member is positioned in between the top sheet and the absorbent body, overlaps with the absorbent body in the thickness direction, and is not joined to the absorbent body.

2. The absorbent article according to claim 1, wherein the supporting portion includes the heat welding portion which has predetermined widths on both sides in the width direction at the folding line.

3. The absorbent article according to claim 2, wherein the supporting portion includes the heat welding portion which is formed from one end portion to the other end portion in the longitudinal direction of the supporting portion.

4. The absorbent article according to claim 1, wherein the folding line overlaps with at least a portion of the absorbent body in the thickness direction.

5. The absorbent article according to claim 1, further comprising:
a joining target portion which is joined to the ventral side waist region in the absorbent main body, and is to be a target of joining the pair of side flaps when being worn,
wherein the folding line overlaps with the joining target portion in the thickness direction.

\* \* \* \* \*